US008278100B2

(12) United States Patent
Pommier et al.

(10) Patent No.: US 8,278,100 B2
(45) Date of Patent: Oct. 2, 2012

(54) LASONOLIDE COMPOUNDS AS REAGENTS FOR INDUCING PREMATURE CHROMOSOME CONDENSATION AND METHODS FOR TREATING DISORDERS

(75) Inventors: Yves Pommier, Bethesda, MD (US); Yongwei Zhang, Germantown, MD (US); Arun K. Ghosh, West Lafayette, IN (US)

(73) Assignee: The United States of America, as Represented by the Secretary of the Department of Health and Human Services, Washington, DC (US)

( * ) Notice: Subject to any disclaimer, the term of this patent is extended or adjusted under 35 U.S.C. 154(b) by 276 days.

(21) Appl. No.: 12/462,005

(22) Filed: Jul. 28, 2009

(65) Prior Publication Data

US 2010/0041619 A1 Feb. 18, 2010

Related U.S. Application Data

(60) Provisional application No. 61/137,193, filed on Jul. 28, 2008.

(51) Int. Cl.
*C12N 5/071* (2010.01)
*G01N 33/48* (2006.01)
*C07D 321/00* (2006.01)
(52) U.S. Cl. ............................ 435/366; 436/63; 549/267
(58) Field of Classification Search .................... 549/267
See application file for complete search history.

(56) References Cited

U.S. PATENT DOCUMENTS

| 5,554,617 | A | * | 9/1996 | Stringfellow et al. ......... 514/272 |
| 5,684,036 | A | * | 11/1997 | Horton et al. .................. 514/450 |
| 5,789,164 | A | | 8/1998 | Gotoh | |
| 6,107,285 | A | * | 8/2000 | Gatti et al. ...................... 514/34 |
| 6,110,679 | A | | 8/2000 | Gotoh | |
| 7,115,756 | B2 | | 10/2006 | Wright et al. | |
| 7,521,474 | B2 | | 4/2009 | Wright et al. | |
| 2004/0132037 | A1 | | 7/2004 | Prasanna et al. | |
| 2006/0264499 | A1 | | 11/2006 | Wright et al. | |

OTHER PUBLICATIONS

Berge et al., "Pharmaceutical Salts", Journal of Pharmaceutical Sciences, (1977) 66(1): 1-19.
Brown et al., Int. J. Radiat. Oncol. Biol. Phys. (1992) 24: 279-286.
Caplus STN Structure Search, Batch printed: Feb. 17, 2009, 68 pages.
Ghosh and Gong, Organic Letters, (2007) 9(8): 1437-1440.
Jennings et al., "Efforts towards the total synthesis of (-)-lasonolide A," Thursday, Nov. 2, 2006, 10:40 am (Augusta Marriot Hotel and Suites), 4 pages.
Robbins and Angell, Basic Pathology, 2nd Edition, W.B. Saunders Co., Philadelphia, 1976, pp. 69-105.
Muller et al., "Biological Indicators for Radiation Damage", Int. J. Radiat. Biol., 1991, 59(4): 863-73 Abstract Only (1 page).
Pantelias et al., "Direct Analysis of Radiation-Induced Chromosome Fragments and Rings in Unstimulated Human Peripheral Blood Lymphocytes by Means of the Premature Chromosome Condensation Technique", Mutat. Res., 1985, 149(1):67-72 Abstract Only (1 page).
Blakeley et al., "Application of the Premature Chromosome Condensation Assay in Simulated Partial-Body Radiation Exposures: Evaluation of the Use of an Automated Metaphase-Finder", Stem Cells, 1995, 13 Suppl 1:223-30 Abstract Only (1 page).
Prasanna et al., "Premature Chromosome Condensation Assay for Biodosimetry: Studies with Fission-Neutrons", Health Phys., 1997, 72(4):594-600 Abstract Only (1 page).
Pantelias et al., "A Simple Method for Premature Chromosome Condensation Induction in Primary Human and Rodent Cells Using Polyethylene Glycol", Somatic Cell Genet., 1983, 9(5):533-547 Abstract Only (1 page).
Gotoh et al., "Detection and Evaluation of Chromosomal Aberrations Induced by High Doses of Gamma-Irradiation Using Immunogold-Silver Painting of Prematurely Condensed Chromosomes", Int. J. Radiat. Biol, 1996, 70(5): 517-520 Abstract Only (1 page).
Durante et al., "A Simple Method for Simultaneous Interphase-Metaphase Chromosome Analysis in Biodosimetry", Int. J. Radiat. Biol., 1998, 74(4): 457-62 Abstract Only (1 page).
Coco-Martin et al., "Detection of Radiation-Induced Chromosome Aberrations Using Fluorescence in Situ Hybridization in Drug-Induced Premature Chromosome Condensations of Tumour Cell Lines with Different Radiosensitivities", Int. J. Radiat. Biol., 1997, 71(3):265-273 Abstract Only (1 page).
Kanda et al., "Easy Biodosimetry for High-Dose Radiation Exposures Using Drug-Induced, Prematurely Condensed Chromosomes", Int. J. Radiat. Biol., 1999, 75(4):441-6 Abstract Only (1 page).

* cited by examiner

*Primary Examiner* — Elli Peselev
(74) *Attorney, Agent, or Firm* — Cantor Colburn LLP

(57) ABSTRACT

The present invention is directed towards lasonolide derivatives, methods of inducing premature chromosome condensation using lasonolide derivatives, and methods of treating disorders, such as cancer, in a subject, the method comprising administering to the subject a lasonolide derivative.

8 Claims, 10 Drawing Sheets
(6 of 10 Drawing Sheet(s) Filed in Color)

**p<0.01; *p<0.05

Green: phosphorylated-Histone H3 (Ser28)
Red: DNA a,b), Cells seeded in top chamber together with drug 6 h;
c,d), Cells attached first in top chamber, then drug 4h.

LASONOLIDE COMPOUNDS AS REAGENTS FOR INDUCING PREMATURE CHROMOSOME CONDENSATION AND METHODS FOR TREATING DISORDERS

CROSS REFERENCE TO RELATED APPLICATION

This application claims the benefit of U.S. Provisional Application No. 61/137,193 filed Jul. 28, 2008, which is hereby incorporated by reference in its entirety.

STATEMENT OF GOVERNMENTAL INTEREST

This invention was funded by the National Cancer Institute at the National Institutes of Health. The United States Government has certain rights in this invention.

BACKGROUND

Chromosomal analysis is a technique used for screening or the diagnosis of genetic diseases, in an assay of the mutagenicity of physical or chemical factors, and other various cytogenetical purposes in medical, biological, agricultural or other fields. Chromosomes are obtained usually from mitotic cells using colhitin or its derivative, colcemid, thereby inhibiting the assembly of tubulin to form mitotic spindles during mitotic process. Therefore it requires cells to pass through mitosis. However, it is well known by those skilled in the art, that it is often difficult to obtain chromosomes in the case in which cells are not proliferate well.

Furthermore, many phenomena occur during interphase; for example, chromosomal cleavage by irradiation and subsequent reunion occur through the interphase nuclei, resulting in chromosomal damage. Thus, it has been required to establish a technique that allows one to obtain chromosomes from interphase cells.

Muller and Streffer (Muller et al. (1991) Int. J. Radiat. Biol. 59, 863-873) published a comprehensive review of biological indicators of radiation damage, explaining current techniques of biological dosimetry for radiation dose assessment. After exposure to high doses of radiation, sufficient numbers of mitotic cells are not available for dose assessment by the routine metaphase spread chromosome aberration analysis. The premature chromosome condensation (PCC) assay, performed on an exposed individual's blood lymphocytes, is viewed as a rapid biodosimetry method of clinical significance (Pantelias et al. (1985) Mutat. Res. 149, 67-72; Blakely et al. (1995) Stem Cells 13, 223-230; and Prasanna et al. (1997) Health Phys. 72, 594-600.

Currently, physical damage to chromosomes can be analyzed by observation of chromosomes after preparation of a metaphase spread. Chromosomes are visualized in mitotic cells following a short-term cell culture in which cells are stimulated into proliferation by a mitogen and then subjected to cell cycle arrest with colchicine or colcemid. The chromosomes are observed under a microscope after being treated either by staining or by hybridizing with a fluorescent probe. This technique depends upon the successful stimulation of the cells to proliferate and requires 48 hours or more of cell culture to obtain useful yields. The technique is labor intensive and requires experience in cytogenetic techniques to practice. The analysis is further complicated by cell killing and cell cycle delay induced by the treatment. In addition, the low yield of condensed chromosomes frequently requires large numbers of metaphase spreads to obtain statistically significant data.

Another method of analyzing physical damage to chromosomes involves inducing the premature chromosome condensation (PCC) in the cells and preparing a chromosome spread. Historically, premature chromosome condensation was accomplished by fusing the cells of interest with mitotic cells. This resulted in the condensation of the chromosomes in the test cells into chromatid-like structures. Although this technique does produce premature chromosome condensation, there are several difficulties associated with its practice. The technique requires a constant supply of mitotic cells to be fused with the test cells. The culture and maintenance of the mitotic cells adds considerably to the expense of the method. Additionally, cell fusion techniques (for example, PEG mediated fusion) are inefficient and produce low and variable yields of fused cells. This results in a low and variable yield of premature chromosome condensation in the test cells (Pantelias et al. (1983) Somatic Cell Genet. 9, 533-547).

The deficiencies of mitotic cell fusion to induce premature chromosome condensation are well known in the art and the search for alternative simple and rapid protocols has been a topic of ongoing research (Gotoh et al. (1996) Int. J. Radiat. Biol. 70, 517-520; Kanda et al. (1999) Int. J. Radiat. Biol. 75, 441-446; Durante et al. (1998) Int. J. Radiat. Biol. 74, 457-462; and Coco-Martin et al. (1997) Int. J. Radiat. Biol. 71, 265-273). Recently, premature chromosome condensation has been induced by stimulating cells with a mitogen and then culturing the cells in the presence of phosphatase inhibitors. Inhibitors of type 1 and 2A protein phosphatases have been used to induce PCC in proliferating cells (Gotoh et al. (1996) Int. J. Radiat. Biol. 70, 517-520; Kanda et al. (1999) Int. J. Radiat. Biol. 75, 441-446; Durante et al. (1998) Int. J. Radiat. Biol. 74, 457-462; and Coco-Martin et al. (1997) Int. J. Radiat. Biol. 71, 265-273).

The condensed chromosomes prepared by phosphatase inhibitor treatment were evaluated for biological dosimetry applications using chromosome aberration analysis in PCC spreads. Premature chromosome condensation was induced by okadaic acid (OA) (Gotoh et al. (1996) Int. J. Radiat. Biol. 70, 517-520; Kanda et al. (1999) Int. J. Radiat. Biol. 75, 441-446) or calyculin A (Durante et al. (1998) Int. J. Radiat. Biol. 74, 457-462) in mitogen stimulated cells and obtained 48 hours after mitogen-stimulation. Durante et al. (Durante et al. (1998) Int. J. Radiat. Biol. 74, 457-462) demonstrated that simultaneous measurement of chromosome aberrations in $G_1$ and M phases is possible by using whole-chromosome probe fluorescence in situ hybridization (FISH) technique following exposure to 200-kVp x-rays. It has also been shown that incubation of actively dividing tumor cell lines in a cell culture medium containing OA or calyculin A results in PCC induction (Coco-Martin et al. (1997) Int. J. Radiat. Biol. 71, 265-273). Using whole-chromosome-specific probes, chemically induced PCC spreads containing radiation-induced chromosome aberrations are readily identified as cells with more than 2 chromosome spots. A difference in radiosensitivity was demonstrated between radiosensitive (SCC61) and radioresistant (A549) cell lines (Coco-Martin et al. (1997) Int. J. Radiat. Biol. 71, 265-273).

Although the use of phosphatase inhibitors produces premature chromosome condensation in stimulated or proliferating cells, presently available methods still require an incubation period in order to produce sufficiently high yields of premature chromosome condensation to be useful for chromosome aberration analysis. The current invention addresses the shortcomings in inducing PCC and in the treatment of certain disorders.

BRIEF SUMMARY OF THE INVENTION

The invention is directed towards lasonolide compounds and the use as a potent inducer of premature chromosome condensation and inhibitor of cell adhesion.

The present invention has been investigated in view of the above-mentioned drawbacks inherent to the prior art, and accordingly, one object of the present invention is to provide an improved PCC technique for obtaining chromosomes prematurely from the interphase cells at any time of cell cycle, with quickly, easily, efficiently and in a highly reproducible manner.

In one aspect, the invention provides a method of modulating chromosome condensation in a subject, the method comprising administering to the subject a lasonolide derivative.

In another aspect, the invention provides a method of inducing chromosome condensation in a subject, the method comprising administering to the subject a compound of formula I:

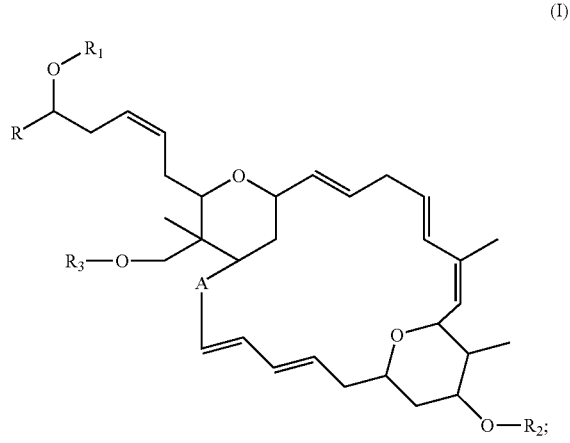

(I)

wherein
each A is independently C(O)O, OC(O), N($R^A$), O, S, S(O), S(O)$_2$, C(O), C(S), C(N$R^A$), C(O)N$R^A$, OC(O)O, O—C($R^A$)$_2$, N($R^A$)C($R^A$)$_2$, or S(O)$_2$—C($R^A$)$_2$;

R is H or A-R';

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

In certain aspects, the invention provides a method of treating a chromosome condensation-related disorder in a subject, comprising administering to said subject in need thereof, an effective amount of a lasonolide derivative or a compound or pharmaceutical composition of formula I.

In another aspect, the invention provides a method of treating a subject suffering from or susceptible to a cell proliferative disorder or disease comprising: administering to the subject an effective amount of a lasonolide derivative or a compound or pharmaceutical composition of formula I.

In one aspect, the invention provides a method of treating cancer in a subject identified as in need of such treatment, the method comprising administering to said subject an effective amount of a lasonolide derivative or a compound or pharmaceutical composition of formula I.

In another aspect, the invention provides a method of inducing chromosome condensation comprising contacting administering to mammalian cells a lasonolide derivative or a compound or pharmaceutical composition of formula I.

In another aspect, the invention provides a method of generating condensed chromosomes by premature chromosome condensation (PCC), which comprises treating proliferating cells with a lasonolide derivative or a compound or pharmaceutical composition of formula I.

In certain aspects, the invention provides a method of analyzing human cell chromosomes by causing premature chromosome condensation, which comprises: a) applying an effective amount of a lasonolide derivative or a compound or composition of formula I to human cells, thereby causing premature chromosome condensation; and b) analyzing the chromosomes treated in step a).

In a related aspect, the invention provides a method of analyzing a chromosome, comprising: (a) incubating a cell with a medium comprising a lasonolide derivative or a compound or compositions of formula I having mitosis enhancing properties, wherein the lasonolide derivative or compound of composition of formula I is present in an amount effective to induce premature chromosome condensation; and (b) analyzing the condensed chromosome.

In one aspect, the invention provides a compound of formula I:

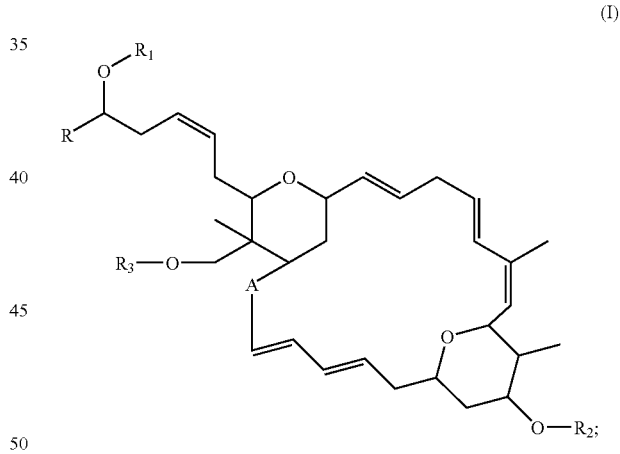

(I)

wherein
each A is independently C(O)O, OC(O), N($R^A$), O, S, S(O), S(O)$_2$, C(O), C(S), C(N$R^A$), C(O)N$R^A$, OC(O)O, O—C($R^A$)$_2$, N($R^A$)C($R^A$)$_2$, or S(O)$_2$—C($R^A$)$_2$;

R is H or A-R';

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

In another aspect, the invention provides a compound of formula II:

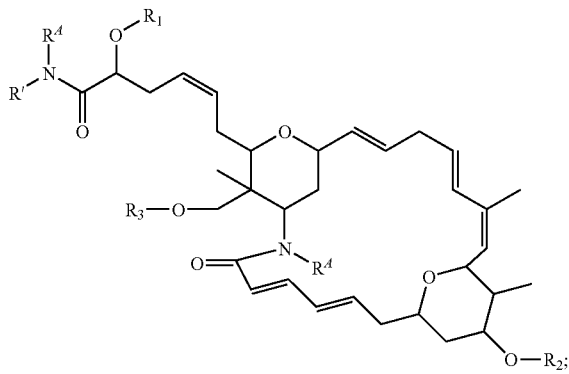

(II)

wherein

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

In still another aspect, the invention provides a compound of formula III:

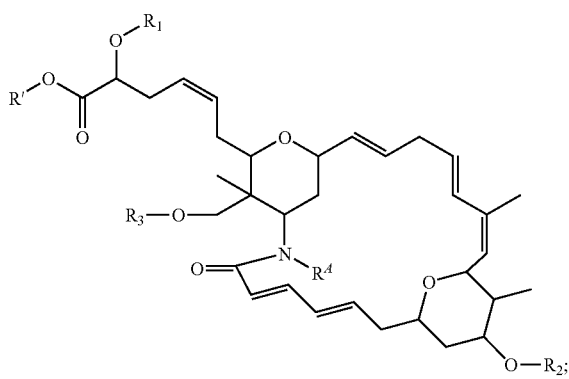

(III)

wherein

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

The invention also provides a compound of formula IV:

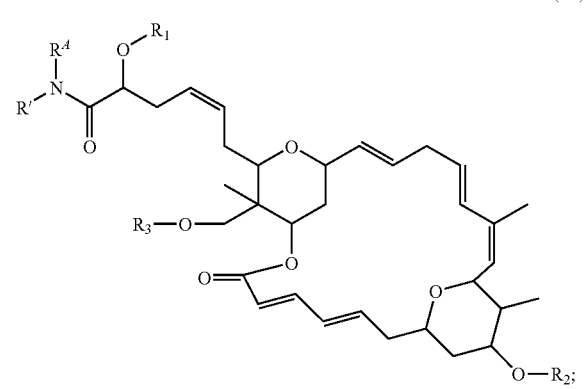

(IV)

wherein

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

The invention also provides a kit comprising an effective amount of a lasonolide derivative or a compound or pharmaceutical composition of formula I:

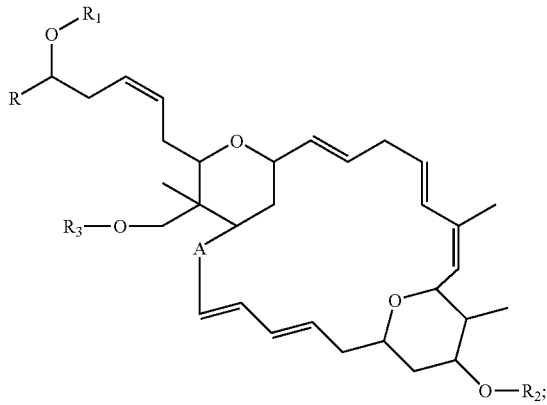

wherein
each A is independently C(O)O, OC(O), N($R^4$), O, S, S(O), S(O)$_2$, C(O), C(S), C(N$R^4$), C(O)N$R^4$, OC(O)O, O—C($R^4$)$_2$, N($R^4$)C($R^4$)$_2$, or S(O)$_2$—C($R^4$)$_2$;

R is H or A-R';

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^4$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

in unit dosage form, together with instructions for administering the compound to a subject suffering from cancer.

In another aspect, the invention provides a pharmaceutical composition comprising a lasonolide derivative or a compound of formula I:

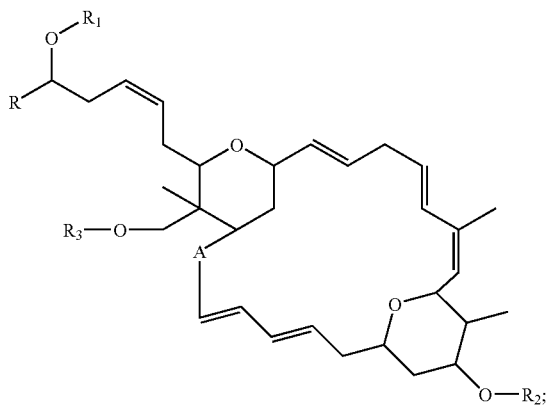

wherein
each A is independently C(O)O, OC(O), N($R^4$), O, S, S(O), S(O)$_2$, C(O), C(S), C(N$R^4$), C(O)N$R^4$, OC(O)O, O—C($R^4$)$_2$, N($R^4$)C($R^4$)$_2$, or S(O)$_2$—C($R^4$)$_2$;

R is H or A-R';

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^4$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

and a pharmaceutically acceptable carrier.

In another aspect, the invention provides a culture medium for inducing premature chromosome condensation in a cell comprising a lasonolide derivative or a compound or composition of formula I having mitosis enhancing properties, wherein the lasonolide derivative or a compound or composition of formula I is present in an amount effective to induce premature chromosome condensation.

In certain aspects, the invention provides a composition comprising a cell and a cell culture medium comprising a lasonolide derivative or a compound or composition of formula I having mitosis enhancing properties, wherein the lasonolide derivative or a compound or composition of formula I is present in an amount effective to induce premature chromosome condensation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiment of this disclosure are further illustrated by the following Figures.

DETAILED DESCRIPTION

Method of Inducing PCC

Figure 1A:
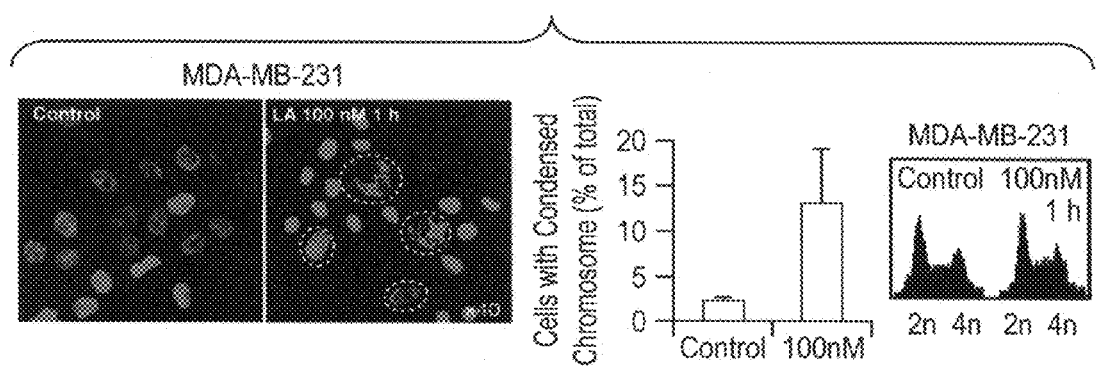
FIG. 1. Lasonolide A induces premature chromosome condensation: With non-toxicity concentration and short-time treatment, Lasonolide A induced premature chromosome condensation (PCC) both in human breast cancer MDA-MB-231 cells (A) and Burkitt's Lymphoma CA46 cells (B) with the treatment at 100 nM for 1 h. DNase I Sensitivity Assay demonstrated there was condensation appearing on chromatins. The phase fluorescence wavelength shift provides evidence of an effect at 100 nM, while at 200 nM a greater change, affecting signal amplitude, is observed. (C). The chromosome spread assay showed that Lasonolide A can induce PCC in each phase of the cell cycle (D and E).
Figure 1B:
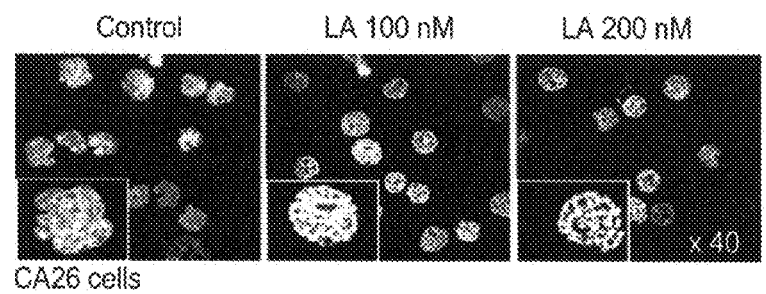

In one aspect, the invention provides a method of modulating chromosome condensation in a subject, the method comprising administering to the subject a lasonolide derivative.

In one embodiment, the subject is identified as being in need of chromosome condensation modulation, and the lasonolide derivative is administered to the identified subject. In another embodiment, the modulation is stimulation.

In another aspect, the invention provides a method of inducing chromosome condensation in a subject, the method comprising administering to the subject a compound of formula I:

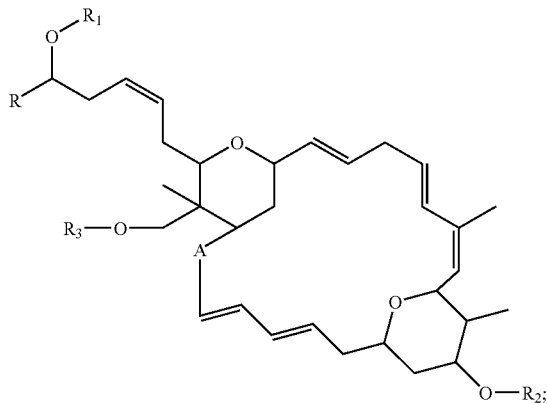

(I)

wherein each A is independently C(O)O, OC(O), N($R^A$), O, S, S(O), S(O)$_2$, C(O), C(S), C(N$R^A$), C(O)N$R^A$, OC(O)O, O—C($R^A$)$_2$, N($R^A$)C($R^A$)$_2$, or S(O)$_2$—C($R^A$)$_2$;

R is H or A-R';

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

In one embodiment, the compound of formula I is selected from:

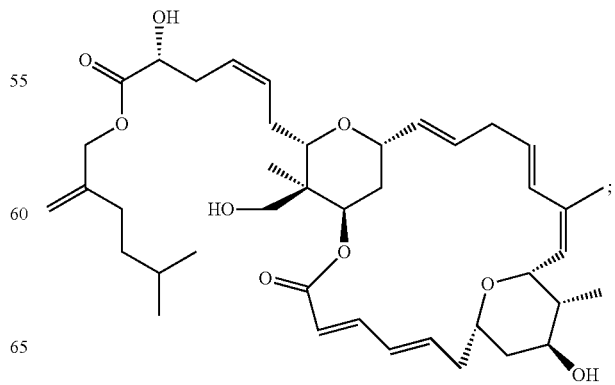

(-)-Lasonolide A

Lasonolide A

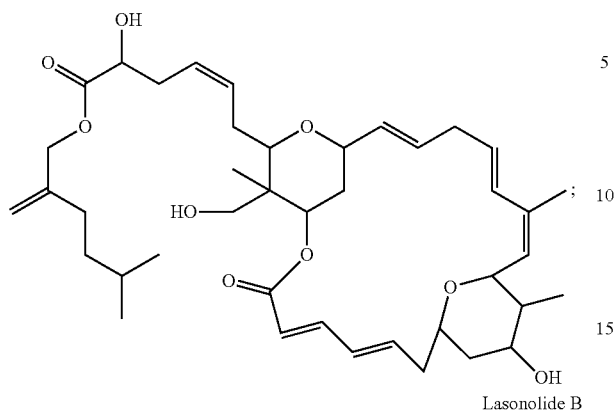

Lasonolide B

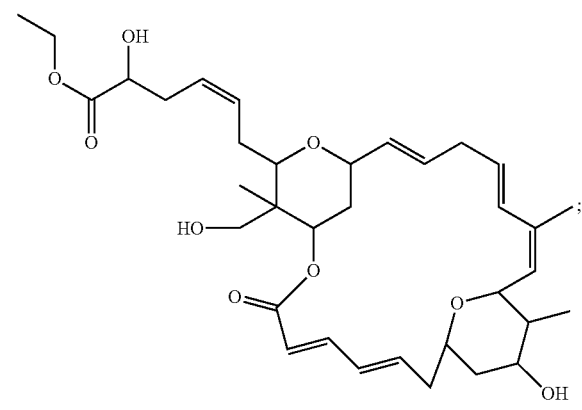

Lasonolide C

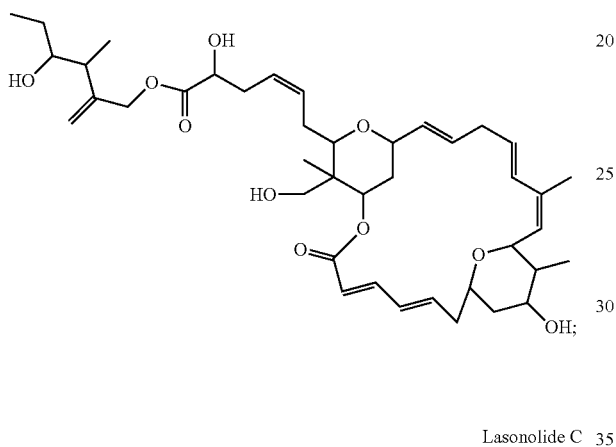

Lasonolide D

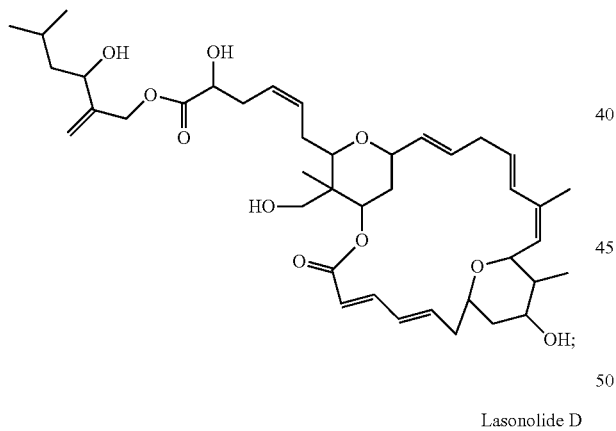

Lasonolide E

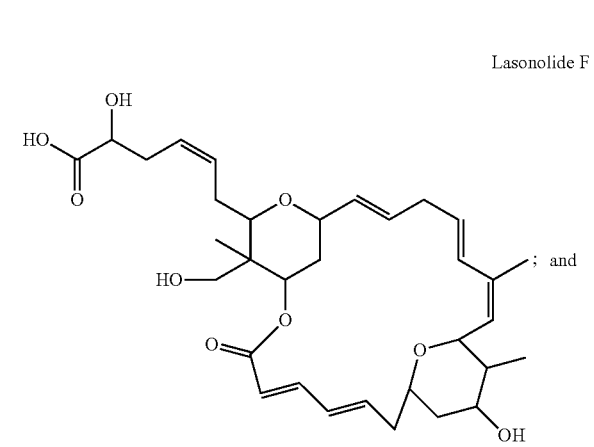

Lasonolide F

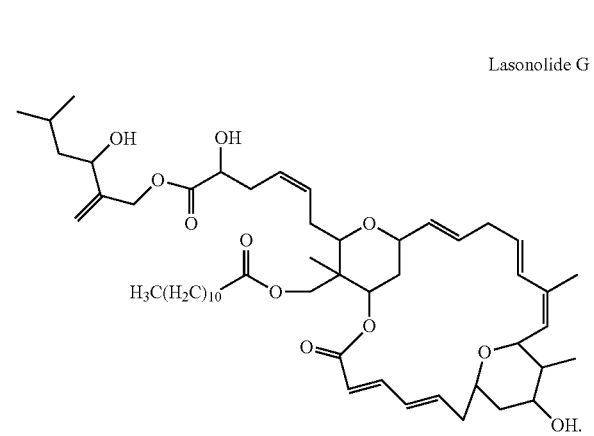

; and

Lasonolide G

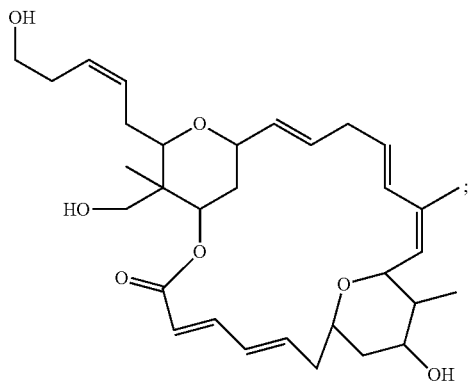

In one embodiment, the subject is identified as being in need of chromosome condensation modulation, and the compound of formula I is administered to the identified subject.

In another embodiment, the compound is determined from a screening assay. In a further embodiment, the screening assay is a chromosome spread assay, a DNase I sensitivity assay, a phosphatase activity assay, an immunofluorescence assay, a cell adhesion assay, or a transwell migration assay.

In another aspect, the invention provides a method of inducing chromosome condensation, the method comprising contacting administering to mammalian cells a lasonolide derivative or a compound or pharmaceutical composition of formula I:

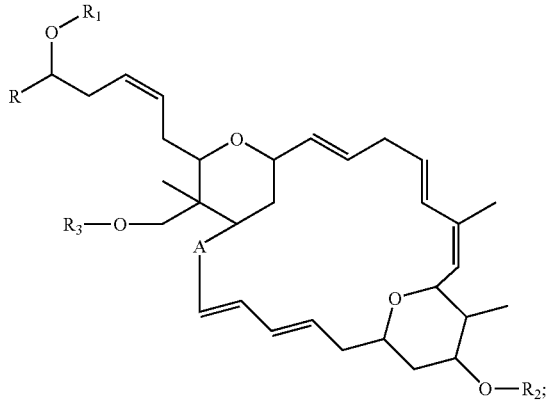

wherein
each A is independently C(O)O, OC(O), N($R^4$), O, S, S(O), S(O)$_2$, C(O), C(S), C(N$R^4$), C(O)N$R^4$, OC(O)O, O—C($R^4$)$_2$, N($R^4$)C($R^4$)$_2$, or S(O)$_2$—C($R^4$)$_2$;

R is H or A-R';

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^4$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

In one embodiment, the cells are contacted in vitro. In another embodiment, the cells are contacted in vivo.

In another aspect, the invention provides a method of generating condensed chromosomes by premature chromosome condensation (PCC), which comprises treating proliferating cells with a lasonolide derivative or a compound or pharmaceutical composition of formula I

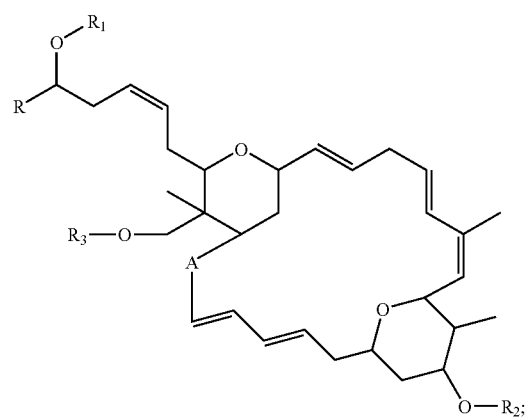

wherein
each A is independently C(O)O, OC(O), N($R^4$), O, S, S(O), S(O)$_2$, C(O), C(S), C(N$R^4$), C(O)N$R^4$, OC(O)O, O—C($R^4$)$_2$, N($R^4$)C($R^4$)$_2$, or S(O)$_2$—C($R^4$)$_2$;

R is H or A-R';

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^4$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

In one embodiment, a concentration of lasonolide A is from 1 to 100 nM.

In another embodiment, the proliferating cells are human cells.

In other embodiments, the proliferating cells are animal cells.

In one aspect, the invention provides a method of analyzing human cell chromosomes by causing premature chromosome condensation, which comprises: a) applying an effective amount of a lasonolide derivative or a compound or pharmaceutical composition of formula I to human cells, thereby causing premature chromosome condensation; and b) analyzing the chromosomes treated in step a).

In another aspect, the invention provides a method of analyzing a chromosome, comprising: (a) incubating a cell with a medium comprising a lasonolide derivative or a compound or pharmaceutical composition of formula I having mitosis enhancing properties, wherein the lasonolide derivative or a compound or pharmaceutical composition of formula I is present in an amount effective to induce premature chromosome condensation; and (b) analyzing the condensed chromosome.

In certain embodiments, analyzing the chromosome comprises preparing a chromosome spread.

In another embodiment, analyzing the chromosomes comprises hybridizing an oligonucleotide to at least one or more chromosomes and enumerating chromosome spots.

In a further embodiment, the oligonucleotide comprises a detectable moiety. In another further moiety, the detectable moiety is a fluorescent moiety.

In other embodiments, the detectable moiety is selected from a group consisting of biotin, digoxigenin, antigens, enzymes and haptens.

In another aspect, the invention provides a culture medium for inducing premature chromosome condensation in a cell comprising a lasonolide derivative or a compound or pharmaceutical composition of formula I having mitosis enhancing properties, wherein the lasonolide derivative or a compound or pharmaceutical composition of formula I is present in an amount effective to induce premature chromosome condensation.

In one embodiment, the lasonolide is A, B, C, D, E, F, or G.

In another embodiment, the invention provides a culture medium further comprising a phosphatase inhibitor. In a further embodiment, the phosphatase inhibitor is selected from a group consisting of okadaic acid, salts of okadaic acid, calyculin A, cantharidic acid, cantharidin, cypermethrin, deltamethrin, dephostatin, 3,4-dephostatin, endothall, fenvalerate, fostriecin, microcystin-LA, microcystin-LF, microcystin-LR, microcystin-LW, microcyctin-RR, and microcystin-YR.

In another aspect, the invention provides a composition comprising a cell and a cell culture medium comprising a lasonolide derivative or a compound or pharmaceutical composition of formula I having mitosis enhancing properties, wherein the lasonolide derivative or a compound or pharmaceutical composition of formula I is present in an amount effective to induce premature chromosome condensation.

In one embodiment, the invention provides a composition further comprising a phosphatase inhibitor.

In certain embodiments, the lasonolide compound or compound of formula I is determined from a screening assay. In a further embodiment, the screening assay is a chromosome spread assay, a DNase I sensitivity assay, a phosphatase activity assay, an immunofluorescence assay, a cell adhesion assay, or a transwell migration assay.

In any aspects, embodiments, and methods described herein, the aspect, embodiment, or method may comprise an energy source, preferably ATP and/or GTP.

In any aspects, embodiments, and methods described herein, the aspect, embodiment, or method may be practiced on any type of cell. In some embodiments, the cell may be a lymphocyte. Preferably, the cell is a mammalian cell. In some embodiments, the cell is a human peripheral blood lymphocyte. In some embodiments, the cell is a murine cell, preferably a murine peripheral blood lymphocyte.

The lasonolide derivative may be effective at any stage of the cell cycle: G1 (Gap 1 phase), S (DNA synthesis phase), G2 (Gap 2 phase) or M (mitosis phase).

The present invention also provides a method for generating chromosomes by PCC which comprises treating proliferating cells with an agent which inhibits protein phosphatases and induces PCC which agent comprises at least one lasonolide. In certain embodiments, the lasonolide derivative is dissolved in a solvent.

In one embodiment, the lasonolide derivative is lasonolide A, B, C, D, E, F, or G.

In one embodiment, the concentration of lasonolide derivative ranges from about 1 to about 100 nM.

In another embodiment, the concentration of lasonolide derivative may be either (i) higher than 100 nM and such that it can generate G1 phase, S phase or G2 phase PCC; or (ii) in the range of about 1 to about 10 nM and such that it can generate G2 phase PCC.

In another embodiment, the concentration of lasonolide derivative may be either (i) higher than 10 nM and such that it can generate G1 phase, S phase or G2 phase PCC; or (ii) 1 nM and able to generate G2 phase PCC.

In certain embodiments, the lasonolide derivative may be for chromosomal analysis of human cells for clinical or medical purposes. In other embodiments, the lasonolide derivative may be for chromosomal analysis of non-human cells.

Notwithstanding the methods discussed above, there exists a need in the art for rapid and simple methods to assess genetic material. Presently, a major cause of the difficulty in making such assessments is the time and labor required to generate condensed chromosomes for subsequent analysis. In one aspect, the invention provides a cell culture medium that induces premature chromosome condensation rapidly and in high yields in unstimulated cells. The present invention does not require the need for cell fusion to induce premature chromosome condensation in unstimulated cells and does not require the need for stimulation and subsequent incubation required by other methods known in the art. Condensed chromosomes prepared using the materials and methods of the present invention have been used to demonstrate that damage to specific chromosomes in unstimulated HPBL can be studied by FISH with whole-chromosome-specific probes in chemically induced PCC spreads. The methods of the present invention are simpler and faster than those known in the art and are particularly suited to automated, high throughput assays of chromosome damage. These methods have numerous applications including rapid biological dosimetry applications.

In one embodiment a method for chromosome condensation in a cell comprises contacting the cell with a lasonolide derivative, including a compound of formula (I) as described herein, and observing chromosome condensation in the cell. The cell may be contacted in vivo or in vitro, though methods of in vitro chromosome condensation are particularly contemplated. In certain embodiments the lasonolide derivative is present at a concentration of about 1 nM to about 500 nM, or about 10 nM to about 200 nM. The cell is contacted with the lasonolide derivative for a period of about 30 minutes to about 24 hours prior to observing the chromosome condensation. Observation may be via a direct method such as a chromosome spread assay (see FIG. 1 and the description related to this figure), or via an indirect method such as a DNase sensitivity assay, cell adhesion assay, transwell migration assay, or thymidine or BrdU incorporation assay. In certain embodiments of this method, 10 to 99% of contacted cells exhibit premature chromosome condensation (PCC), preferably at least 30% of contacted cells exhibit PCC, more preferably at least 50% of contacted cells exhibit PCC, and still more preferably at least 75% of contacted cells exhibit PCC. It is to be understood, however, that any statistically significant increase in PCC relative to control cells not contacted with the lasonolide derivative is a positive result.

In one embodiment, the present invention provides a cell culture medium for inducing premature chromosome condensation in a cell. In preferred embodiments, the cell culture medium comprises one or more mitosis enhancing factors. In some embodiments, the mitosis-enhancing factor may be one or more lasonolides. In a preferred embodiment, the mitosis-enhancing factor is one of lasonolides A-G.

In one embodiment, the invention provides for a cell culture medium comprising a phosphatase inhibitor. In such cases, the phosphatase inhibitor may include one or more lasonolide derivatives.

In certain embodiments, the present invention provides a method of analyzing a chromosome by incubating a cell with a medium comprising a mitosis-enhancing factor, wherein the medium induces premature chromosome condensation, and analyzing the condensed chromosome. In some embodiments, the mitosis-enhancing factor may be one or more lasonolide derivatives.

In another embodiment, the invention provides a medium for use in the method of analyzing a chromosome may comprise a phosphatase inhibitor. Preferably, the phosphatase inhibitor may be one or more lasonolide derivatives.

In certain embodiments, the invention provides a method for analyzing a chromosome, which may be practiced on any type of cell. In some embodiments, the cell may be a lymphocyte. Preferably, the cell is a mammalian cell. In some embodiments, the cell is a human peripheral blood lymphocyte. In some embodiments, the cell is a murine cell, preferably a murine peripheral blood lymphocyte.

In one embodiment, the method of analyzing a chromosome may include preparing a chromosome spread. The method may include hybridizing one or more oligonucleotides to one or more chromosomes and enumerating chromosome spots. In some embodiments, one or more of the oligonucleotides comprises a detectable moiety. Preferably, the detectable moiety is a fluorescent moiety although the detectable moiety may be one or more of biotin, digoxigenin, antigens, enzymes, and haptens.

The present invention also provides a method of assessing clastogenicity of a compound by contacting a cell with the compound, incubating the cell with a medium comprising a mitosis enhancing factor, wherein the medium induces premature chromosome condensation and analyzing the condensed chromosomes for breakage, structural and/or numerical aberrations. In some embodiments, the cell is contacted with the medium and the compound simultaneously. In other embodiments, the cell may be contacted with the compound and then transferred to a suitable medium. It may be desirable in some instances to incubate the cell after contact with the compound for a period of time sufficient to allow chromosomal repair. In some embodiments, the mitosis-enhancing factor may be one or more lasonolide derivatives.

A medium for use in the method of assessing clastogenicity of a compound may comprise a phosphatase inhibitor. Preferably, the phosphatase inhibitor may be one or more lasonolide derivatives.

The method of assessing clastogenicity of a compound may include preparing a chromosome spread. The method may include hybridizing one or more oligonucleotides to one or more chromosomes and enumerating chromosome spots. In some embodiments, one or more of the oligonucleotides comprises a detectable moiety. Preferably, the detectable moiety is a fluorescent moiety although the detectable moiety may be one or more of biotin, digoxigenin, antigens, enzymes, and haptens.

In another embodiment, the present invention also provides a method of assessing toxicity of a compound by contacting a cell with the compound, incubating the cell with a medium comprising a mitosis enhancing factor, wherein the medium induces premature chromosome condensation and analyzing the condensed chromosomes. In some embodiments, the cell is contacted with the medium and the compound simultaneously. In other embodiments, the cell may be contacted with the compound and then transferred to a suitable medium. It may be desirable in some instances to incubate the cell after contact with the compound for a period of time sufficient to allow chromosomal repair. In some embodiments, the mitosis-enhancing factor may be one or more lasonolide derivatives.

A medium for use in the method of assessing toxicity of a compound may comprise a phosphatase inhibitor. Preferably, the phosphatase inhibitor may be one or more lasonolide derivatives.

The method of assessing toxicity of a compound may include preparing a chromosome spread. The method may include hybridizing one or more oligonucleotides to one or more chromosomes and enumerating chromosome spots. In some embodiments, one or more of the oligonucleotides comprises a detectable moiety. Preferably, the detectable moiety is a fluorescent moiety although the detectable moiety may be one or more of biotin, digoxigenin, antigens, enzymes, and haptens.

In another embodiment, the present invention also provides a method of detecting chromosomal abnormalities in a subject by isolating one or more cells from the subject, incubating the cell with a medium comprising a mitosis enhancing factor, wherein the medium induces premature chromosome condensation and analyzing the condensed chromosomes for abnormalities. In some embodiments, the mitosis-enhancing factor may be one or more lasonolide derivatives.

A medium for use in the method of detecting chromosomal abnormalities in a subject may comprise a phosphatase inhibitor. Preferably, the phosphatase inhibitor may be one or more of lasonolide derivatives.

The method of detecting chromosomal abnormalities in a subject may include preparing a chromosome spread. The method may include hybridizing one or more oligonucleotides to one or more chromosomes and enumerating chromosome spots. In some embodiments, one or more of the oligonucleotides comprises a detectable moiety. Preferably, the detectable moiety is a fluorescent moiety although the detectable moiety may be one or more of biotin, digoxigenin, antigens, enzymes, and haptens.

The present invention also provides a method of assessing a radiation dose received by a subject by isolating one or more cells from the subject, contacting one or more cells with a medium comprising a mitosis enhancing factor, wherein the medium induces premature chromosome condensation and analyzing the condensed chromosomes for abnormalities such as breakage, structural and/or numerical aberrations. In some embodiments, the mitosis-enhancing factor may be one or more lasonolide derivatives.

A medium for use in the method of assessing a radiation dose received by a subject may comprise a phosphatase inhibitor. Preferably, the phosphatase inhibitor may be one or more lasonolide derivatives.

The method of assessing a radiation dose received by a subject may include preparing a chromosome spread. The method may include hybridizing one or more oligonucleotides to one or more chromosomes and enumerating chromosome spots. In some embodiments, one or more of the oligonucleotides comprises a detectable moiety. Preferably, the detectable moiety is a fluorescent moiety although the detectable moiety may be one or more of biotin, digoxigenin, antigens, enzymes, and haptens.

In certain embodiments, the present invention provides materials and methods for the induction of premature chromosome condensation without the need to stimulate the cells with a mitogen. In addition, the present invention provides methods of analyzing genetic material by inducing premature chromosome condensation and analyzing the physical structure of the condensed chromosomes. The present invention is useful in any application requiring premature chromosome condensation in a test cell. The invention is particularly useful in the fields of cytogenetics, molecular cytogenetics, cell biology, genetic toxicology, and genomics.

In some aspects, the present invention provides materials and methods useful in diagnostic cytogenetics. The materials and methods of the present invention may be used in prenatal, postnatal and pre-implantation testing to evaluate the genetic material of a test cell. For example, the methods described herein may be used to evaluate the genetic material in a potential sperm donor to determine the presence or absence of chromosomal aberrations in the sperm. Likewise, the present invention may be used to analyze the genetic material of a subject while the subject is in utero.

In some related aspects, the present invention can be used in cytogenetic research. In the field of genomics, for example, the present invention may be used to detect genes associated with various syndromes characterized by chromosomal aberrations. In a particular embodiment, the present invention may be used to detect genes associated with microdeletion syndromes. In another embodiment, the present invention may be used to detect chromosomal anomalies (both numerical and structural) associated with cancer. In some preferred embodiments, the present invention may be used to detect gene amplification.

In the field of environmental testing, the present invention may be used to assess the exposure of a subject to radiation. The radiation dose may have been received as a result of accidental exposure or may be the result of occupational exposure. The present invention may be particularly useful in cases of exposure of a large number of subjects as the capability of automating the present invention makes it well suited to a high throughput automated screening system. In other embodiments, the exposure of a subject to a compound, which induces chromosomal abnormalities, can be assessed.

In some preferred embodiments, the present invention provides methods of assessing the toxicity of a drug. These methods are useful in the identification of potential chemotherapeutic agents where it is desirable to have an agent capable of inducing chromosomal breaks. In this aspect, the present methods may be used to assess the clastogenicity (ability to break chromosomes) of a particular agent. The present methods may also be used as an initial safety screen to determine whether a therapeutic agent induces chromosomal aberrations.

The present invention provides a cell culture medium for inducing premature chromosome condensation in a test cell. Any suitable cell culture medium may be supplemented with one or more mitosis enhancing factors to be used as a cell culture medium of the invention. A suitable cell culture medium is one in which the cell of interest may be maintained in a viable state throughout the duration of the induction of premature chromosome condensation. Optionally, the suitable cell culture medium may be one in which the test cell may be maintained for a protracted period of time.

The cell culture media of the present invention will typically comprise various ingredients selected to maintain the viability of the test cells. Such ingredients include, but are not limited to, amino acids, vitamins inorganic salts, buffers or buffer salts, sugars, lipids, trace elements, cytokines and hormones.

In preferred embodiments, a cell culture medium of the present invention will comprise one or more mitosis enhancing factors. Mitosis enhancing factors are agents associated with the progression of the cell cycle into mitosis. The mitosis enhancing may be one or more lasonolide derivatives. In preferred embodiments, the mitosis-enhancing factor may be a purified mitosis-enhancing factor. The mitosis-enhancing factor may be purified to any desired level of purity. Preferably, the mitosis enhancing factor will at least 50% pure, i.e., the mitosis enhancing factor will make up at least 50% by weight of a mitosis-enhancing-factor containing material to be added to a culture medium. In other preferred embodiments, a mitosis enhancing factor may be 75% or greater pure, 80% or greater pure, 85% or greater pure, 90% or greater pure or 95% or greater pure. In a preferred embodiment, a cell culture medium of the present invention may comprise lasonolide derivatives.

A cell culture medium of the present invention may optionally comprise one or more transfection reagents. As used herein, transfection reagent is seen to include any reagent which, when added to a cell culture medium, enhances the uptake by a test cell of a mitosis enhancing factor. Transfection reagents include, but are not limited to, neutral lipids, cationic lipids, mixtures of neutral and cationic lipids, proteins, peptides, lipoproteins, lipopeptides, and the like. The transfection reagent may be added directly to the media or may be combined with the mitosis-enhancing factor prior to the addition of the mitosis-enhancing factor to the medium.

A cell culture medium of the present invention may optionally comprise one or more phosphatase inhibitors. In some preferred embodiments, the protein phosphatases may specifically inhibit serine/threonine protein phosphatases. In some preferred embodiments the phosphatase inhibitors may specifically inhibit the protein phosphatases 1 and 2A. Suitable protein phosphatases include lasonolide derivatives.

The cell culture media of the present invention may be used to formulate cell culture compositions comprising a cell or cell population and a culture medium of the invention. The cell may be any cell in which it is desired to induce premature chromosome condensation. Cells isolated from subjects are particularly preferred. The isolated cells may be derived from any organ or tissue in the subject including, but not limited to, blood, heart, lung, epithelial tissue and/or intestinal tissue.

The present invention also provides a composition comprising a cell and a cell culture medium, wherein the cell culture medium comprises a mitosis-enhancing factor and induces premature chromosome condensation in the cell. In the compositions of the present invention, the mitosis enhancing may be one or more lasonolide derivatives. The compositions of the present invention may include a phosphatase inhibitor. The phosphatase inhibitor may be one or more lasonolide derivatives.

Any type of cell having genetic material may be used in the practice of the present invention. For example, cells from heart, lung, liver, kidney, brain, or other tissue may be used as a source of cells. The isolation of cells from various tissues may be accomplished using any technique known to those skilled in the art. In preferred embodiments, the cells are of mammalian origin, such as human or murine cells. In some preferred embodiments, peripheral blood lymphocytes may be used for premature chromosome condensation and analysis. In other preferred embodiments, cells may be oocytes, obtained from embryos, amniotic fluid, or established cell lines, such as stem cell lines.

The isolation of the cells to be used in the present invention may be by any means known to those skilled in the art. In some preferred embodiments, human peripheral blood lymphocytes (HPBLs) may be used. The isolation of peripheral blood lymphocytes is routine in the art. One suitable protocol is described below and other methods known to those skilled in the art could be used. In the following protocol, the peripheral blood lymphocytes were isolated from a human subject. They could equivalently be isolated from any subject. In some preferred embodiments, the subject may be mammalian. In other preferred embodiments, the subject may be a human or a mouse.

Treatment of Diseases

In one aspect, the invention provides a method of treating a chromosome condensation-related disorder in a subject, comprising administering to said subject in need thereof, an effective amount of a lasonolide derivative or a compound or pharmaceutical composition of formula I:

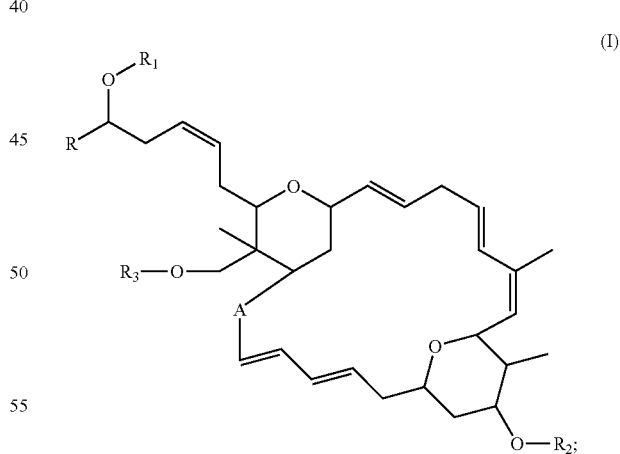

wherein each A is independently C(O)O, OC(O), N($R^4$), O, S, S(O), S(O)$_2$, C(O), C(S), C(N$R^4$), C(O)NR A, OC(O)O, O—C($R^4$)$_2$, N($R^4$)C($R^4$)$_2$, or S(O)$_2$—C($R^4$)$_2$;

R is H or A-R';

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

In certain aspects, the invention provides a method of treating a subject suffering from or susceptible to a cell proliferative disorder or disease comprising: administering to the subject an effective amount of a lasonolide derivative or a compound or pharmaceutical composition of formula I:

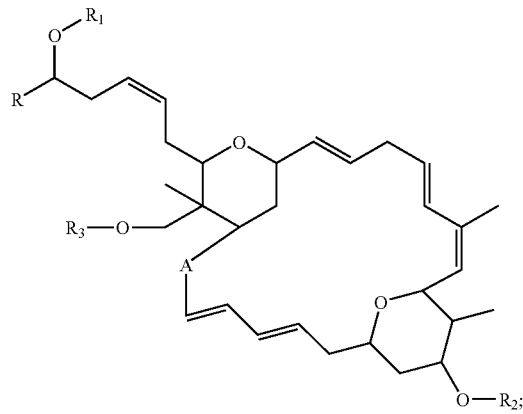

(I)

wherein
each A is independently C(O)O, OC(O), N($R^A$), O, S, S(O), S(O)$_2$, C(O), C(S), C(N$R^A$), C(O)N$R^A$, OC(O)O, O—C($R^A$)$_2$, N($R^A$)C($R^A$)$_2$, or S(O)$_2$—C($R^A$)$_2$;

R is H or A-R';

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

In one embodiment, the disorder is cancer, tumor, neoplasm, neovascularization, vascularization, cardiovascular disease, intravasation, extravasation, metastasis, arthritis, infection, Alzheimer's disease, blood clot, atherosclerosis, melanoma, skin disorder, rheumatoid arthritis, diabetic retinopathy, macular edema, or macular degeneration, inflammatory and arthritic disease, or osteosarcoma.

In another aspect, the invention provides a method of treating cancer in a subject identified as in need of such treatment, the method comprising administering to said subject an effective amount of a lasonolide derivative or a compound or pharmaceutical composition of formula I:

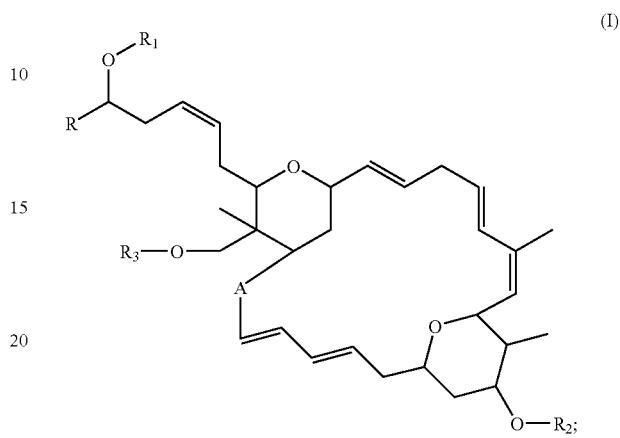

(I)

wherein
each A is independently C(O)O, OC(O), N($R^A$), O, S, S(O), S(O)$_2$, C(O), C(S), C(N$R^A$), C(O)N$R^A$, OC(O)O, O—C($R^A$)$_2$, N($R^A$)C($R^A$)$_2$, or S(O)$_2$—C($R^A$)$_2$;

R is H or A-R';

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

In one embodiment, the subject is suffering from a solid tumor or disseminated cancer.

In certain embodiments, the compound or composition is administered in combination with other anti-cancer or anti-tumor therapeutics.

In a further embodiment, the other anti-cancer or anti-tumor therapeutics are selected from antibiotics, nitrogen mustards, pyrimidine analogs, and steroid compounds.

In another further embodiment, the compound or composition is administered in combination with a topoisomerase inhibitor. In certain embodiments, the topoisomerase inhibitor is a topoisomerase II inhibitor. The topoisomerase inhibitor is selected from etoposide, doxorubicin, daunorubicin, mitoxantrone, ellipticines, acridines, camptothecin, camptothecin derivatives, morpholinodoxorubicin, pyrazoloacridine, and rubidazone.

In another embodiment, the step of administering the compound comprises administering the compound orally, topically, parentally, intravenously or intramuscularly.

In other embodiments, the method comprises the step of administering an effective amount of a composition comprising a compound of formula I and a pharmaceutically suitable excipient.

In certain embodiments, the subject is a mammal. In certain embodiments, the subject is a primate or human, preferably a human.

In another embodiment, the step of administering the compound of formula I comprises administering the compound in a dosage of between about 0.01 µg/kg/day and 100 mg/kg/day.

Tumors or neoplasms include new growths of tissue in which the multiplication of cells is uncontrolled and progressive. Some such growths are benign, but others are termed "malignant," leading to death of the organism. Malignant neoplasms or "cancers" are distinguished from benign growths in that, in addition to exhibiting aggressive cellular proliferation, they invade surrounding tissues and metastasize. Moreover, malignant neoplasms are characterized in that they show a greater loss of differentiation (greater "dedifferentiation"), and of their organization relative to one another and their surrounding tissues. This property is also called "anaplasia."

Neoplasms treatable by the present invention include all solid tumors, i.e., carcinomas and sarcomas, including Kaposi's sarcoma. Carcinomas include those malignant neoplasms derived from epithelial cells, which tend to infiltrate (invade) the surrounding tissues and give rise to metastases. Adenocarcinomas are carcinomas derived from glandular tissue or in which the tumor cells form recognizable glandular structures. Sarcoma, including Kaposi's sarcoma, broadly includes tumors whose cells are embedded in a fibrillar or homogeneous substance like embryonic connective tissue. However, it will be understood that the method of the invention is not limited to the treatment of these tumor types, but extends to any solid tumor derived from any organ system.

Thus, the treatable cancers include, for example, colon cancer, bladder cancer, breast cancer, melanoma, ovarian carcinoma, prostatic carcinoma, or lung cancer, and a variety of other cancers as well. The invention is especially useful in the inhibition of cancer growth in adenocarcinomas, including, for example, those of the prostate, breast, kidney, ovary, testes, and colon. The invention is further useful against melanomas, which derive from the melanocytic system in the skin and other organs.

A solid tumor can be malignant, e.g. tending to metastasize and being life threatening, or benign. Examples of solid tumors that can be treated according to a method of the present invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Moreover, tumors comprising dysproliferative changes (such as metaplasias and dysplasias) are treated or prevented in epithelial tissues such as those in the cervix, esophagus, and lung. Thus, the present invention provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68-79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, Medicine, 2d Ed., J. B. Lippincott Co., Philadelphia.

Other examples of tumors that are benign and can be treated with a method of the present invention include arteriovenous (AV) malformations, particularly in intracranial sites and myoleomas. A method of the present invention may also be used to treat psoriasis, a dermatologic condition that is characterized by inflammation and vascular proliferation; benign prostatic hypertrophy, a condition associated with inflammation and possibly vascular proliferation; and cutaneous fungal infections. Treatment of other hyperproliferative disorders is also contemplated.

In certain embodiments, the present invention is directed to a method for inhibiting cancer growth, including processes of cellular proliferation, invasiveness, and metastasis in biological systems. Preferably, the method is employed to inhibit or reduce cancer cell proliferation, invasiveness, metastasis, or tumor incidence in living animals, such as mammals.

The invention includes a method of inducing cytotoxicity (cell killing) in cancer cells or reducing the viability of cancer cells. For example, the invention can be used to induce cytotoxicity in cells of carcinomas of the prostate, breast, ovary, testis, lung, colon, or breast. The selective killing of the cancer cells can occur through apoptosis, necrosis, another mechanism, or a combination of mechanisms.

The killing of cancer cells can occur with less cytotoxicity to normal cells or tissues than is found with conventional cytotoxic therapeutics, preferably without substantial cytotoxicity to normal cells or tissues. For example, the lasonolides identified in the instant invention can induce cytotoxicity in cancer cells while producing little or substantially no cytotoxicity in normal cells. Thus, unlike conventional cytotoxic anticancer therapeutics, which typically kill all growing cells, the lasonolides can produce differential cytotoxicity: tumor cells are selectively killed whereas normal cells are spared. Thus, in another embodiment, the invention is a method for inducing differential cytotoxicity in cancer cells relative to normal cells or tissue. This differential in cytotoxicity associated with the steroid compounds occurs as a result of apoptosis, necrosis, another mechanism, or a combination of such mechanisms.

The compounds of the invention exhibit their cancer treatment properties at concentrations that lead to fewer side effects than those of known chemotherapeutic agents, and in some cases are substantially free of side effects. The compounds of the invention are useful for extended treatment protocols, where other compounds would exhibit undesirable side effects. In addition, it is believed that the properties of hydrophilicity and hydrophobicity are well balanced in these compounds, enhancing their utility both in vitro and especially in vivo, while other compounds lacking such balance are of substantially less utility. Specifically, the compounds have an appropriate degree of solubility in aqueous media to permit absorption and bioavailability in the body, while also having a degree of solubility in lipids to permit traversal of the cell membrane to a putative site of action. The compounds are maximally effective if they can be delivered to the site of the tumor and are able to enter the tumor cells.

In the treatment of certain localized cancers, the degree of hydrophilicity of the compounds of the invention can be of lesser importance. The compounds of the invention that may have low solubility in aqueous systems, can be used in direct or topical treatment of skin cancers, e.g., melanoma or basal cell carcinoma, or by implantation into the brain to topically treat brain cancer.

The compounds of the invention are effective to inhibit the proliferation, invasiveness, or metastasis of cancer cells in vitro, as well as in vivo. These compounds possess an excellent balance of properties, in that they are shown to possess unusually strong activity in inhibiting the cancer growth, including proliferation, invasiveness, or metastasis of cancer cells. Another advantage is that it has an unexpectedly long serum half-life. Therefore, certain compounds of the invention may only require periodic administration, e.g., once or twice per week.

The method can be used as a prophylactic treatment, e.g., by administering the lasonolide compound to a mammal after detection of a gene product or metabolite associated with predisposition to a cancer but before any specific cancerous lesion is detected. Alternatively, the lasonolide compounds are useful for preventing cancer recurrence, for example, to treat residual cancer following surgical resection or radiation therapy.

The effect occurs over a wide range of concentrations, including at concentrations that are extraordinarily low. The amount of the compounds of the invention used according to the invention is an amount that is effectively inhibitory of cancer growth. An amount of compounds of the invention is effectively inhibitory to cancer growth if it significantly reduces cellular proliferation or the potential of invasiveness or metastasis. Proliferation refers to the capacity of a tumor to increase its volume through cell division, typically measured as the "doubling rate." The inhibition of cellular proliferation by the present method means that the rate of growth is decreased. In some cases, the method can actually induce regression or diminution of tumor mass, if the rate of replenishment of the tumor cells through cell division is exceeded by the rate of cell death. Invasiveness refers to the potential of a tumor or tumor cells to invade other tissues, typically by breaking down the extracellular matrix of those tissues. Metastasis refers to the potential of a tumor or tumor cells to establish new tumor foci at sites distant from the primary site where the tumor began. Typically, metastasis proceeds by individual cells or groups of cells breaking off from the primary tumor and migrating, e.g., through the blood or lymph, to establish a new tumor focus in another tissue or organ. One locus common in tumor metastasis is in the lung, where the very fine vasculature of the lung tissue can often catch circulating tumor cells, permitting the establishment of a tumor focus therein. Some types of tumors metastasize to specific types of tissues.

The cancers treatable by means of the present invention occur in mammals. Mammals include, for example, humans, as well as pet animals such as dogs and cats, laboratory animals such as rats and mice, and farm animals such as horses and cows.

Assays to Determine Compounds of the Invention

To determine the mechanism of lasonolide compounds as anti-tumor candidates, a number of assays were performed. First, premature chromosome condensation (PCC) was induced by Lasonolide A within 1 h at nanomolar concentrations. In breast cancer MDA-MB-231 cells, Lasonolide A induced PCC in the 13% of cells at 1 h. In Burkitt's lymphoma CA 46 cells, 100 nM Lasonolide A for 1 h led to chromosome condensation in the 97.9% of cells. By chromosome spread assay, Lasonolide A was shown to induce PCC in each phases of cell cycle. Additionally, the effect of Lasonolide A on PCC induction was reversible. Compared with the classical inducer of PCC, Okadaic Acid, Lasonolide A showed a more potent ability of PCC induction both in tumor cells and normal human lymphocytes. Using DNA synthesis inhibitor and Cycline-dependent kinase (CDK) inhibitors, it was found that PCC induced by Lasonolide A was independent from DNA replication and CDK activity. However, Lasonolide A decreased the acetylation of histone H3 Lysine 9. In addition, the histone deacetylase inhibitor, suberoylanilide hydroxamic acid (SAHA) inhibited partially the PCC induction of Lasonolide A in CA 46 cells, which suggested that histone deacetylation might be involved in Lasonolide A-induced PCC. Second, in breast cancer MDA-MB-231, MCF-7 cells, colon cancer HT 29, HCT 116 cells and Burkitt's lymphoma CA 46 cells, G2/M phase arrest was found after 24 h treatment of Lasonolide A. BrdU incorporation assay showed that Lasonolide A decelerated DNA replication in MDA-MB-231, MCF-7 and CA 46 cells. Third, Lasonolide A also inhibited adhesion of MDA-MB-231 cells at nanomolar concentration, and reorganized the cytoskeleton system. The attachment of MDA-MB-231 cells to extracellular matrices such as collagen I and fibronectin was blocked by Lasonolide A. Consequently, Lasonolide A inhibited migration of MDA-MB-231 cells.

For experiments involving fluorescent in situ hybridization analysis (FISH), after preparing a chromosome spread, whole-chromosome DNA hybridization probe specific for one or more chromosomes. Optionally, a whole chromosome DNA hybridization probe may be directly labeled with a detectable moiety and may be used to analyze the spread chromosomes. Such labeled chromosome-probes are commercially available.

In situ hybridization and chromosome painting may be done using techniques well known in the art (see, for example, Brown et al. (1992) Int. J. Radiat. Oncol. Biol. Phys. 24, 279-286).

Cells may be mounted in a medium containing 4,6-diamidino-2-phenyl-indole (DAPI) for analyzing chromosome I aberrations under a fluorescence microscope (Leitz) equipped with filters for DAPI and fluorescein isothiocyanate (FITC).

The coded slides may be observed at a 1000× magnification for analyzing aberrations involving chromosome 1.

Chromosome aberration analysis is based on the following general criteria: The cells to be included in the analysis should show one or more (and preferably all) of the following: (a) at least partial separation of chromosomes with condensed chromatin material as determined by DAPI counterstain, (b) two or more clearly separated chromosome 1-specific spots with bright green fluorescent signals (cells with single green spots, arising because of overlapping signals, were not included), (c) spots that were similar in fluorescent intensity, and (d) an area representing about 15 to 100% of the area of the spots observed in samples from sham-treated controls.

The area of spots in the control samples may not always be uniform because of differential chromosome condensation and, in a few cases, angular presentation under the microscope. In such cases of ambiguity, cells should be excluded from analysis.

Compounds of the Invention

In one aspect, the invention provides a compound of formula I:

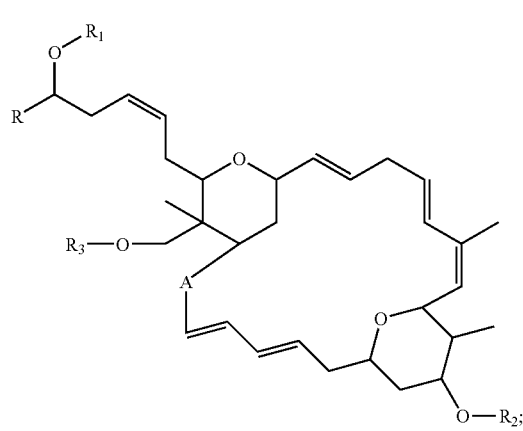

(I)

wherein each A is independently C(O)O, OC(O), N($R^A$), O, S, S(O), S(O)$_2$, C(O), C(S), C(N$R^A$), C(O)N$R^A$, OC(O)O, O—C($R^A$)$_2$, N($R^A$)C($R^A$)$_2$, or S(O)$_2$—C($R^A$)$_2$;

R is H or A-R';

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

In one embodiment, each A is independently C(O)O, OC(O), or N($R^A$), and $R^A$ is H, an optionally substituted alkyl, or an optionally substituted aryl.

In another embodiment, R' is H, an optionally substituted alkyl, an optionally substituted aryl, an optionally substituted heteroaryl, or an optionally substituted aralkyl.

In certain embodiments, $R_1$ and $R_2$ are each H.

In other embodiments, $R_3$ is H or an optionally substituted alkyl, an optionally substituted aryl, an optionally substituted heteroaryl, or an optionally substituted aralkyl.

In another aspect, the invention provides a compound of formula II:

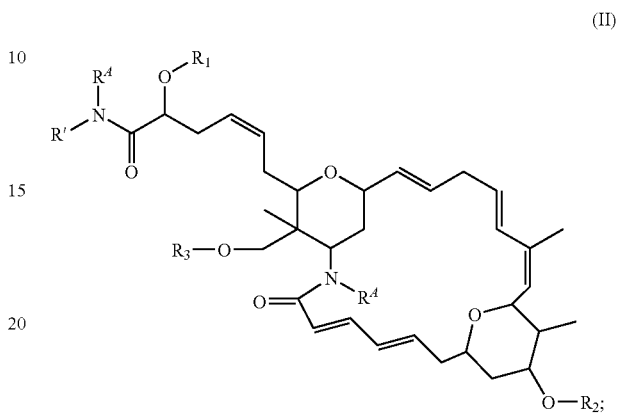

(II)

wherein

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

In still another aspect, the invention provides a compound of formula III:

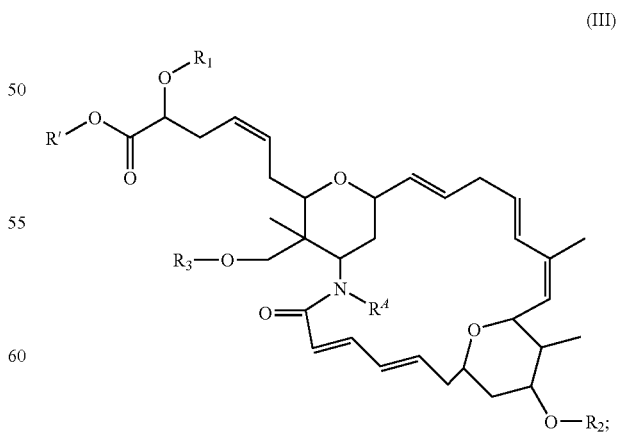

(III)

wherein

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

The invention also provides a compound of formula IV:

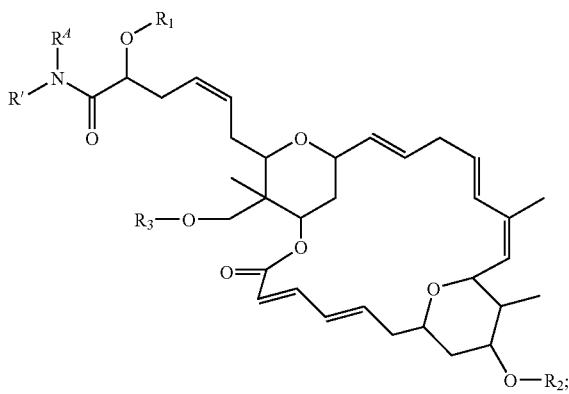

(IV)

wherein

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl.

Other embodiments include the compounds, intermediates, or a pharmaceutically acceptable salt, solvate, clathrate, hydrate, polymorph, or prodrug thereof delineated herein, or compositions including them. Still other embodiments include the compounds or a pharmaceutically acceptable salt, solvate, or hydrate thereof delineated herein, or compositions including them.

Another embodiment is a method of making a compound of any of the formulae herein using any one, or combination of, reactions delineated herein. The method can include the use of one or more intermediates or chemical reagents delineated herein. Methods of synthesizing the compounds of the invention can be found at least in Ghosh, A. K. et al. *Organic Letters*, 2007, 9(8), pp. 1437-1440, the contents of which are expressly incorporated herein by reference.

Acids and bases useful in the methods herein are known in the art. Acid catalysts are any acidic chemical and can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical and can be inorganic (e.g., sodium bicarbonate, potassium hydroxide) or organic (e.g., triethylamine, pyridine) in nature. Bases are useful in either catalytic or stoichiometric amounts to facilitate chemical reactions.

The recitation of a listing of chemical groups in any definition of a variable herein includes definitions of that variable as any single group or combination of listed groups.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Formulation, Administration, Kits, and Pharmaceutical Compositions

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

In one aspect, the invention provides a pharmaceutical composition comprising a lasonolide derivative or a compound or pharmaceutical composition of formula I:

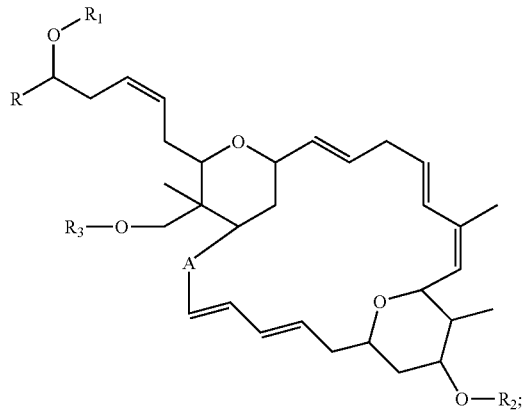

(I)

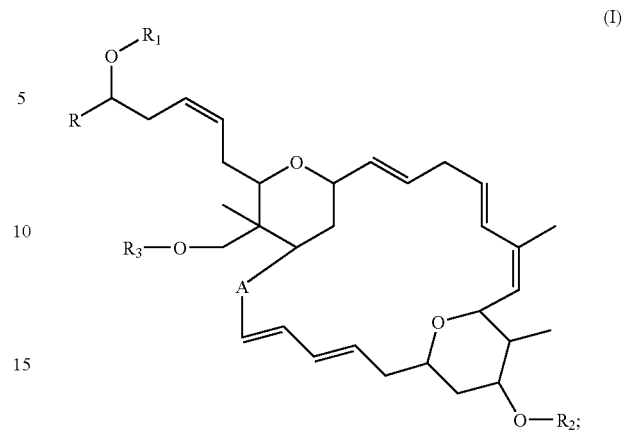

(I)

wherein each A is independently C(O)O, OC(O), N($R^A$), O, S, S(O), S(O)$_2$, C(O), C(S), C(N$R^A$), C(O)N$R^A$, OC(O)O, O—C($R^A$)$_2$, N($R^A$)C($R^A$)$_2$, or S(O)$_2$—C($R^A$)$_2$;

R is H or A-R';

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

and a pharmaceutically acceptable carrier.

In one embodiment, the compound is selected from (−)-Lasonolide A, Lasonolide A, Lasonolide B, Lasonolide C, Lasonolide D, Lasonolide E, Lasonolide F, and Lasonolide G; and a pharmaceutically acceptable carrier.

In another embodiment, the invention provides a pharmaceutical composition further comprising an additional therapeutic agent.

In a further embodiment, the composition is administered in combination with other anti-cancer or anti-tumor therapeutics or a topoisomerase inhibitor. In one aspect, the invention provides a kit comprising an effective amount of a lasonolide derivative or a compound or pharmaceutical composition of formula I:

wherein each A is independently C(O)O, OC(O), N($R^A$), O, S, S(O), S(O)$_2$, C(O), C(S), C(N$R^A$), C(O)N$R^A$, OC(O)O, O—C($R^A$)$_2$, N($R^A$)C($R^A$)$_2$, or S(O)$_2$—C($R^A$)$_2$;

R is H or A-R';

R' is H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

$R_1$, $R_2$, and $R_3$ are each independently H, an optionally substituted alkyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

each $R^A$ is independently H, an optionally substituted alkyl, an optionally substituted alkenyl, an optionally substituted alkynyl, an optionally substituted cycloalkyl, an optionally substituted heterocycloalkyl, an optionally substituted aryl, an optionally substituted heteroaryl, an optionally substituted aralkyl, or an optionally substituted heteroaralkyl;

in unit dosage form, together with instructions for administering the compound to a subject suffering from cancer.

In other aspects, the invention provides a kit comprising an effective amount of a lasonolide derivative in unit dosage form, together with instructions for administering the lasonolide derivative to a subject suffering from cancer.

The phrase "pharmaceutically acceptable" refers to those compounds of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes a pharmaceutically-acceptable material, composition or vehicle, involved in carrying or transporting the subject chemical from one organ, or portion of the body, to another organ, or portion of the body. Each carrier must be "acceptable" in the sense of being compatible with the other ingredients of the formulation and not injurious to the patient.

A therapeutically effective amount can be administered in one or more doses. The term "administration" or "administering" includes routes of introducing the compound(s) to a subject to perform their intended function. Examples of routes of administration that can be used include injection (subcutaneous, intravenous, parenterally, intraperitoneally, intrathecal), oral, inhalation, rectal and transdermal.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically", "peripheral administration" and "administered peripherally" as used herein mean the administration of a compound(s), drug or other material, such that it enters the patient's system and, thus, is subject to metabolism and other like processes, for example, subcutaneous administration.

Methods of preparing these compositions include the step of bringing into association a compound(s) with the carrier and, optionally, one or more accessory ingredients. These compositions may also contain adjuvants such as preservatives, wetting agents, emulsifying agents, and dispersing agents.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. Alternatively, delayed absorption of a parenterally-administered drug form is accomplished by dissolving or suspending the drug in an oil vehicle.

Regardless of the route of administration selected, the compound(s), which may be used in a suitable hydrated form, and/or the pharmaceutical compositions of the present invention, are formulated into pharmaceutically acceptable dosage forms by conventional methods known to those of skill in the art.

In certain embodiments, the pharmaceutical compositions are suitable for topical, intravenous, intratumoral, parental, or oral administration. The methods of the invention further include administering to a subject a therapeutically effective amount of a conjugate in combination with another pharmaceutically active compound. Pharmaceutically active compounds that may be used can be found in *Harrison's Principles of Internal Medicine*, Thirteenth Edition, Eds. T. R. Harrison et al. McGraw-Hill N.Y., NY; and the Physicians Desk Reference 50th Edition 1997, Oradell N.J., Medical Economics Co., the complete contents of which are expressly incorporated herein by reference.

Formulations are provided to a subject in an effective amount. The term "effective amount" includes an amount effective, at dosages and for periods of time necessary, to achieve the desired result. An effective amount of conjugate may vary according to factors such as the disease state, age, and weight of the subject, and the ability of the compound to elicit a desired response in the subject. Dosage regimens may be adjusted to provide the optimum therapeutic response.

The effective amount is generally determined by the physician on a case-by-case basis and is within the skill of one in the art. As a rule, the dosage for in vivo therapeutics or diagnostics will vary. Several factors are typically taken into account when determining an appropriate dosage. These factors include age, sex and weight of the patient, the condition being treated, and the severity of the condition.

Suitable dosages and formulations of immune modulators can be empirically determined by the administering physician. Standard texts, such as Remington: The Science and Practice of Pharmacy, 17th edition, Mack Publishing Company, and the Physician's Desk Reference, each of which are incorporated herein by reference, can be consulted to prepare suitable compositions and doses for administration. A determination of the appropriate dosage is within the skill of one in the art given the parameters for use described herein. Standard texts, such as Remington: The Science and Practice of Pharmacy, 17th edition, Mack Publishing Company, incorporated herein by reference, can be consulted to prepare suitable compositions and formulations for administration, without undue experimentation. Suitable dosages can also be based upon the text and documents cited herein. A determination of the appropriate dosages is within the skill of one in the art given the parameters herein.

In terms of treatment, an effective amount is an amount that is sufficient to palliate, ameliorate, stabilize, reverse or slow the progression of a cancerous disease or otherwise reduce the pathological consequences of the cancer. A therapeutically effective amount can be provided in one or a series of administrations. The effective amount is generally determined by the physician on a case-by-case basis and is within the skill of one in the art.

As a rule, the dosage for in vivo therapeutics or diagnostics will vary. Several factors are typically taken into account when determining an appropriate dosage. These factors include age, sex and weight of the patient, the condition being treated, the severity of the condition and the form of the compound being administered.

Ascertaining dosage ranges is well within the skill of one in the art. The dosage of conjugates can range from about 0.001 µg/kg/day to about 500 mg/kg/day. Methods for administering compositions are known in the art. Such dosages may vary, for example, depending on whether multiple administrations are given, tissue type and route of administration, the condition of the individual, the desired objective, and other factors known to those of skill in the art. Administrations can be conducted infrequently, or on a regular weekly basis until a desired, measurable parameter is detected, such as diminution of disease symptoms. Administration can then be diminished, such as to a biweekly or monthly basis, as appropriate.

Such dosages may vary, for example, depending on whether multiple administrations are given, tissue type and route of administration, the condition of the individual, the desired objective, and other factors known to those of skill in the art.

Following administration of the composition, it can be necessary to wait for the composition to reach an effective tissue concentration at the site of the disorder before detection. Duration of the waiting step varies, depending on factors such as route of administration, location, and speed of movement in the body. In addition, where the compositions are coupled to molecular carriers, the rate of uptake can vary, depending on the level of receptor expression on the surface of the cells. For example, where there is a high level of receptor expression, the rate of binding and uptake is increased. Determining a useful range of waiting step duration is within the level of ordinary skill in the art and may be optimized.

The compounds of the invention useful according to the method of the invention appear to exhibit their beneficial effect in a dose-dependent manner. Thus, within broad limits, administration of larger quantities of a steroid compound has been observed to inhibit cancer cell growth or invasiveness to a greater degree than does administration of a smaller amount. Moreover, efficacy has been observed at dosages below the level at which toxicity is seen in normal cells or at the organism level. Accordingly, one of the advantages of the invention is that the debilitating side effects usually attendant upon conventional cytotoxic cancer treatments are reduced, and preferably avoided.

Available routes of administration include subcutaneous, intramuscular, intraperitoneal, intradermal, oral, intranasal, intrapulmonary (i.e., by aerosol), intravenously, intramuscularly, subcutaneously, intracavity, intrathecally or transdermally, alone or in combination with other pharmaceutical agents.

Compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or liquid aerosol when used with an appropriate aerosolize device. Although not required, compositions are preferably supplied in unit dosage form suitable for administration of a precise amount. Also contemplated by this invention are slow-release or sustained release forms, whereby a relatively consistent level of the active compound are provided over an extended period.

Another method of administration is intravascular, for instance by direct injection into the blood vessel, or surrounding area. Further, it may be desirable to administer the compositions locally to the area in need of treatment; this can be achieved, for example, by local infusion during surgery, by injection, by means of a catheter, or by means of an implant, said implant being of a porous, non-porous, or gelatinous material, including membranes, such as silastic membranes, or fibers.

Although methods and materials similar or equivalent to those described herein can be used in the practice of the present invention, preferred methods and materials are described above. The materials, methods, and examples are illustrative only and not intended to be limiting. Other features and advantages of the invention will be apparent from the detailed description and from the claims.

Enteral administration is a preferred route of delivery of the compound and compositions including the compounds of the invention with appropriate diluents, carriers, and the like are readily formulated. Liquid or solid (e.g., tablets, gelatin capsules) formulations can be employed. It is among the advantages of the invention that, in many situations, the compounds of the invention can be delivered orally, as opposed to parenteral delivery (e.g., injection, infusion) which is typically required with conventional chemotherapeutic agents.

Parenteral use (e.g., intravenous, intramuscular, subcutaneous injection) is also contemplated, and formulations using conventional diluents, carriers, etc., such as are known in the art can be employed to deliver the compound.

Alternatively, delivery of the compounds of the invention can include topical application. Compositions deemed to be suited for such topical use include as gels, salves, lotions, ointments, and the like. In the case of tumors having foci inside the body, e.g., brain tumors, the steroid compound can be delivered via a slow-release delivery vehicle, e.g., a polymeric material, surgically implanted at or near the lesion situs.

The maximal dosage for a subject is the highest dosage that does not cause undesirable or intolerable side effects. For the purpose of the present invention, side effects may include clinically significant antimicrobial or antibacterial activity, as well as toxic effects. The practitioner is guided by skill and knowledge in the field, and the present invention includes, without limitation, dosages that are effective to achieve the described phenomena.

The present invention provides kits for the induction of premature chromosome condensation in test cells. In some embodiments, the kits may comprise one or more containers of a cell culture medium, which comprises a mitosis-enhancing factor and induces premature chromosome condensation in the cell. The mitosis enhancing may be one or more lasonolide derivatives. The kits of the present invention may include one or more containers holding one or more phosphatase inhibitors. The phosphatase inhibitor may be one or more lasonolide derivatives.

The present invention contemplates kits adapted for use in cytogenetic research. Typically, the kits of the invention may comprise one or more containers holding a cell culture medium of the present invention. The cell culture medium may be in liquid form or in the form of a dry powder concentrate. The kits of the invention may comprise one or more containers holding one or more mitosis enhancing factors. The factors may be in solution or may be in the form of a dried powder. Kits of the invention may comprise one or more containers holding one or more phosphatase inhibitors. Optionally, kits of the invention may comprise one or more containers holding one or more transfection reagents and/or one or more energy sources that may be in solution or in dry form.

Kits of the present invention preferably comprise instructions for inducing premature chromosome condensation using the materials and methods of the present invention. In particular, the instructions may provide detailed protocols for inducing premature chromosome condensation in a cell or cell population without the need to stimulate the cell or cell population with a mitogen.

The invention can also be practiced by including with the compounds of the invention and one or more other anti-cancer chemotherapeutic agents, such as any conventional chemotherapeutic agent. The combination of the compounds of the invention with such other agents can potentiate the chemotherapeutic protocol. Numerous chemotherapeutic protocols will present themselves in the mind of the skilled practitioner as being capable of incorporation into the method of the invention. Any chemotherapeutic agent can be used, including alkylating agents, antimetabolites, hormones and antagonists, radioisotopes, as well as natural products. For example, steroid compound can be administered with antibiotics such as doxorubicin and other anthracycline analogs, nitrogen mustards such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinomas of the breast and prostate, in which the tumors can include gonadotropin-dependent and gonadotropin-independent cells, the compound can be administered in conjunction with leuprolide or goserelin. Other antineoplastic protocols include the use of a lasonolide compound with another treatment modality, e.g., surgery, radiation, other chemotherapeutic agent, etc., referred to herein as "adjunct antineoplastic modalities." Thus, the method of the invention can be employed with such conventional regimens with the benefit of reducing side effects and enhancing efficacy.

The invention can also be practiced by using the compounds of the invention and one or more topoisomerase inhibitors. The term "topoisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topoisomerase II has a similar mechanism of action, which involves the induction of DNA strand breaks or the formation of free radicals. In certain embodiments, the topoisomerase inhibitors are inhibitors of topoisomerase II. Any topoisomerase inhibitors can be used, including but not limited to, etoposide, doxorubicin, daunorubicin, mitoxantrone, ellipticines, and acridines. In certain embodiments, the topoisomerase inhibitors encompass compounds such as camptothecin and camptothecin derivatives, as well as morpholinodoxorubicin. Doxorubicin, pyrazoloacridine, mitoxantrone, and rubidazone are illustrations of topoisomerase II inhibitors.

DEFINITIONS

In order that the invention may be more readily understood, certain terms are first defined and collected here for convenience.

The term "administration" or "administering" includes routes of introducing the compound(s) to a subject to perform their intended function. Examples of routes of administration that can be used include injection (subcutaneous, intravenous, parenterally, intraperitoneally, intrathecal), oral, inhalation, rectal and transdermal.

The term "admixture" refers to something that is produced from mixing.

The language "biological activities" includes all genomic and non-genomic activities elicited by these compounds.

The term "cancer" refers to a malignant tumor of potentially unlimited growth that expands locally by invasion and systemically by metastasis. The term "cancer" also refers to the uncontrolled growth of abnormal cells. Specific cancers are selected from, but not limited to, rhabdomyosarcomas, chorio carcinomas, glioblastoma multiformas (brain tumors), bowel and gastric carcinomas, leukemias, ovarian cancers, prostate cancers, lymphomas, osteosarcomas or cancers which have metastasized.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

A "compound of Formula I" or any of the subformulae thereof such as Formula II, III, or IV, includes pharmaceutically acceptable salts, solvates, clathrates, polymorphs, and hydrates of the compound.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the angiogenesis inhibitor compound are outweighed by the therapeutically beneficial effects.

A therapeutically effective amount of compound (i.e., an effective dosage) may range from about 0.001 µg/kg/day to about 500 mg/kg/day, preferably 0.01 µg/kg/day, and 100 mg/kg/day. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. It will also be appreciated that the effective dosage of a compound used for treatment may increase or decrease over the course of a particular treatment.

The terms "hyperproliferative" and "neoplastic" are used interchangeably, and include those cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The term "modulate" refers to increases or decreases in the activity of a cell in response to exposure to a compound of the invention, e.g., the induction of premature chromosome condensation such that a desired end result is achieved, e.g., a therapeutic result.

The term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the terms neoplasia and hyperplasia can be used interchangeably, as their context will reveal, referring to generally to cells experiencing abnormal cell growth rates. Neoplasias and hyperplasias include "tumors," which may be benign, premalignant, or malignant.

The term "non-direct interaction" refers to any interactions that are neither ionic nor covalent, such as hydrogen bonding or van der Waals interactions.

The term "optionally substituted" can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocycloalkyl, alkylaryl, aryl, or an aromatic or heteroaromatic moiety. It will be understood by those skilled in the art that the moieties substituted as a substituent can themselves be substituted, if appropriate.

In other embodiments, substituents on any group (for example, alkyl, alkenyl, alkynyl, aryl, aralkyl, heteroaryl, heteroaralkyl, cycloalkyl, cyclyl, heterocycloalkyl, and heterocyclyl) can be at any atom of that group, wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of suitable substituents include, but not limited to alkyl, alkenyl, alkynyl, cyclyl, cycloalkyl, heterocyclyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents are alkyl, alkenyl, alkynyl, aryl, aralkyl, heteroaryl, heteroaralkyl, cycloalkyl, cyclyl, heterocycloalkyl, and heterocyclyl and include, without limitation halogen, CN, $NO_2$, $OR^{15}$, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, (=O), (=S), (=$NR^{15}$), $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)H$, $C(O)R^{17}$, $NR^{15}C(O)R^{17}$, $Si(R^{15})_3$, $OSi(R^{15})_3$, $Si(OH)_2R^{15}$, $B(OH)_2$, $P(O)(OR^{15})_2$, $S(O)R^{17}$, or $S(O)_2R^{17}$. Each $R^{15}$ is independently hydrogen, $C_1$-$C_6$ alkyl optionally substituted with cycloalkyl, aryl, heterocyclyl, or heteroaryl. Each $R^{16}$ is independently hydrogen, $C_3$-$C_6$ cycloalkyl, aryl, heterocyclyl, heteroaryl, $C_1$-$C_4$ alkyl, or $C_1$-$C_4$ alkyl substituted with $C_3$-$C_6$ cycloalkyl, aryl, heterocyclyl, or heteroaryl. Each $R^{17}$ is independently $C_3$-$C_6$ cycloalkyl, aryl, heterocyclyl, heteroaryl, $C_1$-$C_4$ alkyl, or $C_1$-$C_4$ alkyl substituted with $C_3$-$C_6$ cycloalkyl, aryl, heterocyclyl, or heteroaryl. Each $C_3$-$C_6$ cycloalkyl, aryl, heterocyclyl, heteroaryl and $C_1$-$C_4$ alkyl in each $R^{15}$, $R^{16}$ and $R^{17}$ can optionally be substituted with halogen, CN, $C_1$-$C_4$ alkyl, OH, $C_1$-$C_4$ alkoxy, COOH, $C(O)OC_1$-$C_4$ alkyl, $NH_2$, $C_1$-$C_4$ alkylamino, or $C_1$-$C_4$ dialkylamino.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "prodrug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "reduced toxicity" is intended to include a reduction in any undesired side effect elicited by a compound when administered in vivo.

The term "sarcoma" is art recognized and refers to malignant tumors of mesenchymal derivation.

The term "subject" refers to animals such as mammals, including, but not limited to, primates (e.g., humans), cows, sheep, goats, horses, dogs, cats, rabbits, rats, mice and the like. In certain embodiments, the subject is a human.

The phrases "systemic administration," "administered systemically", "peripheral administration" and "administered peripherally" as used herein mean the administration of a compound(s), drug or other material, such that it enters the patient's system and, thus, is subject to metabolism and other like processes, for example, subcutaneous administration.

The term "test compound" or "drug candidate" or "modulator" or grammatical equivalents as used herein describes any molecule, e.g., protein, oligopeptide, small organic molecule, polysaccharide, polynucleotide, etc., to be tested for the capacity to directly or indirectly modulate the activity of Tdp1.

The term "therapeutically effective amount" refers to that amount of the compound being administered sufficient to prevent development of or alleviate to some extent one or more of the symptoms of the condition or disorder being treated.

The terms "treating" and "treatment" refer to a method of alleviating or abating a disease and/or its attendant symptoms.

The term "tumor suppressor gene" refers to a gene that acts to suppress the uncontrolled growth of a cancer, such as a tumor.

The term "alkyl" refers to the radical of saturated aliphatic groups, including straight-chain alkyl groups and branched-chain alkyl groups. The term alkyl further includes alkyl groups, which can further include oxygen, nitrogen, sulfur, or phosphorous atoms replacing one or more carbons of the hydrocarbon backbone. In preferred embodiments, a straight chain or branched chain alkyl has 30 or fewer carbon atoms in its backbone (e.g., $C_1$-$C_{30}$ for straight chain, $C_3$-$C_{30}$ for branched chain), preferably 26 or fewer, and more preferably 20 or fewer.

Moreover, the term "alkyl" as used throughout the specification and claims is intended to include both "unsubstituted alkyls" and "substituted alkyls," the latter of which refers to alkyl moieties having substituents replacing a hydrogen on one or more carbons of the hydrocarbon backbone. The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and most preferably from one to four carbon atoms in its backbone structure, which may be straight or branched-chain.

The terms "alkylaryl" or "aralkyl" are used interchangeably, and refer to an alkyl substituted with an aryl (e.g., phenylmethyl (benzyl)), or an aryl group substituted with an alkyl. The term "heteroaralkyl" refers to either an alkylaryl or aralkyl group that is substituted at any number of positions with a heteroatom.

The terms "alkenyl" and "alkynyl" refer to unsaturated aliphatic groups analogous in length and possible substitution to the alkyls described above, but that contain at least one double or triple bond, respectively.

The term "aryl" as used herein, refers to the radical of aryl groups, including 5- and 6-membered single-ring aromatic groups. "Heteroaryl" groups may include from one to four heteroatoms. Examples of aryl and heteroaryl groups include benzene, pyrrole, furan, thiophene, imidazole, benzoxazole, benzothiazole, triazole, tetrazole, pyrazole, pyridine, pyrazine, pyridazine and pyrimidine, and the like. Polycyclic fused aromatic groups such as naphthyl, quinolyl, indolyl, and the like are also contemplated.

Those aryl groups having heteroatoms in the ring structure may also be referred to as "aryl heterocycles," "heteroaryls," or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings that are not aromatic so as to form a polycycle (e.g., tetralin).

The term "chiral" refers to molecules that have the property of non-superimposability of the mirror image partner, while the term "achiral" refers to molecules, which are superimposable on their mirror image partner.

The term "cycloalkyl" refers to the radical of saturated or unsaturated cyclic aliphatic groups, including cycloalkyl (alicyclic) groups, alkyl substituted cycloalkyl groups, and cycloalkyl substituted alkyl groups. The term cycloalkyl further includes cycloalkyl groups, which can further include oxygen, nitrogen, sulfur, or phosphorous atoms replacing one or more carbons of the hydrocarbon backbone. Preferred cycloalkyls have from 3-10 carbon atoms in their ring structure, and more preferably have 3, 4, 5, 6, or 7 carbons in the ring structure.

The term "diastereomers" refers to stereoisomers with two or more centers of dissymmetry and whose molecules are not mirror images of one another.

The term "enantiomers" refers to two stereoisomers of a compound that are non-superimposable mirror images of one another. An equimolar mixture of two enantiomers is called a "racemic mixture" or a "racemate."

The term "halogen" designates —F, —Cl, —Br or —I.

The term "haloalkyl" is intended to include alkyl groups as defined above that are mono-, di- or polysubstituted by halogen, e.g., fluoromethyl and trifluoromethyl.

The term "hydroxyl" means —OH.

The term "heteroatom" as used herein means an atom of any element other than carbon or hydrogen. Preferred heteroatoms are nitrogen, oxygen, sulfur and phosphorus.

The term "heterocycloalkyl" refers to the radical of saturated or unsaturated cyclic aliphatic groups substituted by any number of heteroatoms, including heterocycloalkyl (alicyclic) groups, alkyl substituted heterocycloalkyl groups, and heterocycloalkyl substituted alkyl groups. Heteroatoms include but are not limited to oxygen, nitrogen, sulfur or phosphorous atoms replacing one or more carbons of the hydrocarbon backbone. Preferred heterocycloalkyls have from 3-10 carbon atoms in their ring structure, and more preferably have 3, 4, 5, 6 or 7 carbons in the ring structure, wherein a heteroatom may replace a carbon atom.

The terms "inhibition" and "inhibits" refer to a method of prohibiting a specific action or function.

The term "inhibitor," as used herein, refer to a molecule, compound or complex which blocks or modulates a biological or immunological activity.

The term "isomers" or "stereoisomers" refers to compounds that have identical chemical constitution, but differ with regard to the arrangement of the atoms or groups in space.

The terms "polycyclic group" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

Furthermore the indication of stereochemistry across a carbon-carbon double bond is also opposite from the general chemical field in that "Z" refers to what is often referred to as a "cis" (same side) conformation whereas "E" refers to what is often referred to as a "trans" (opposite side) conformation. With respect to the nomenclature of a chiral center, the terms "d" and "l" configuration are as defined by the IUPAC Recommendations. As to the use of the terms, diastereomer, racemate, epi mer and enantiomer, these will be used in their normal context to describe the stereochemistry of preparations.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Another embodiment is a compound of any of the formulae herein made by a process delineated herein, including the processes exemplified in the schemes and examples herein. Another aspect of the invention is a compound of any of the formulae herein for use in the treatment or prevention in a subject of a disease, disorder or symptom thereof delineated herein. Another aspect of the invention is use of a compound of any of the formulae herein in the manufacture of a medicament for treatment or prevention in a subject of a disease, disorder or symptom thereof delineated herein.

It will be readily apparent to those of skill in the art that other suitable modifications and adaptations may be made to the materials and methods of the present invention without departing from the scope of the invention or any embodiment thereof. Having now described the invention in detail, the invention may be more clearly understood with reference to the figures and the following non-limiting examples.

EXAMPLES

Example 1

PCC induction and PI staining

Burkitt's Lymphoma CA46 cells (500,000) (FIG. 1B) or breast cancer MDA-MB-231 cells (500,000) (FIG. 1A) were treated by 100 nM Lasonolide A (stock solution 100 μM in DMSO) for 1 h. Lymphocytes were treated with 200 nM Lasonolide A for 1 h. Cells were harvested with centrifuging on 2,000 rpm for 5 min at 4° C. Pellets were washed once by PBS and re-suspended in 1 mL PBS. 200 μL cells mixture were added to the chamber for cytospining. Cells were cytospun on 800 rpm for 10 min; slides were fixed in fresh-made 4% paraformaldehyde fixation for 20 min at room temperature, then moved to 70% ethanol for 20 min. Slides were stained with Propidium Iodide ("PI") (20 μg/mL) and RNase A (100 μg/mL) for 15 min. Slides were washed with PBS for three times and mounted with Vectashield anti-fade mounting media (Vector Laboratories, Inc., Burlingame, Calif.). Images were taken using a Nikon Eclipse TE-300 confocal microscope.

Example 2

Chromosome Spread Assay

Figure 1C:
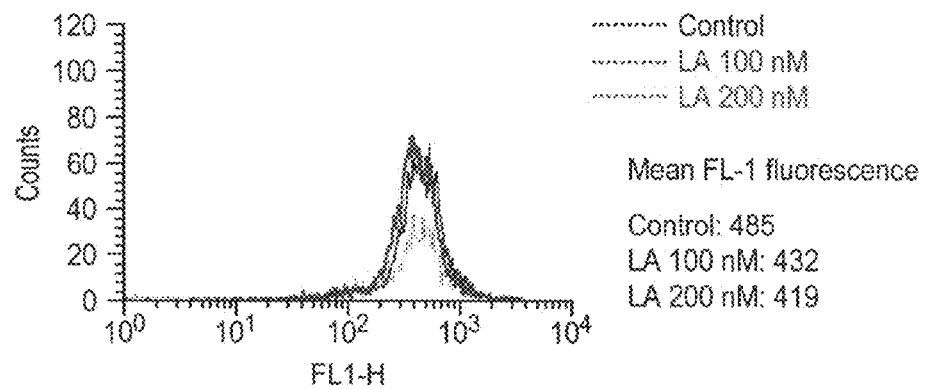
Figure 1D:
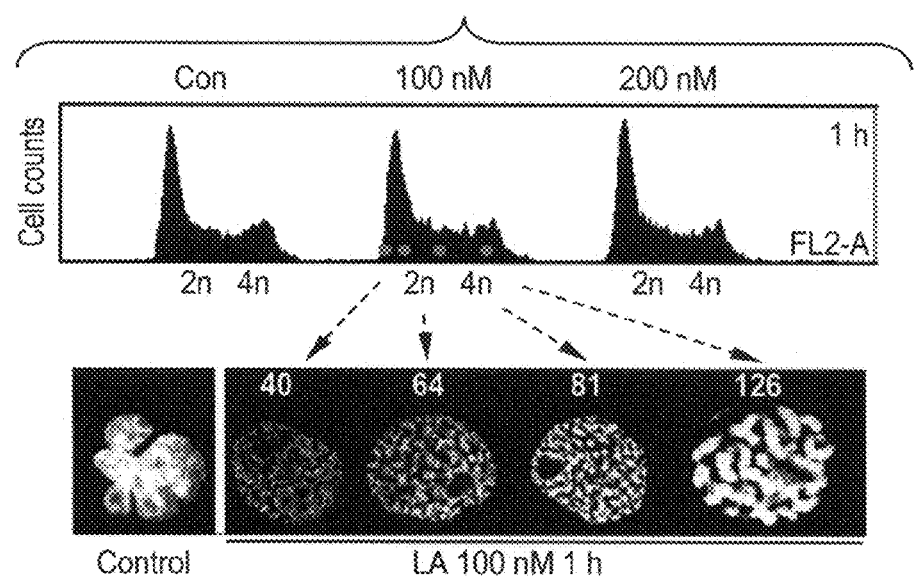
Figure 1E:
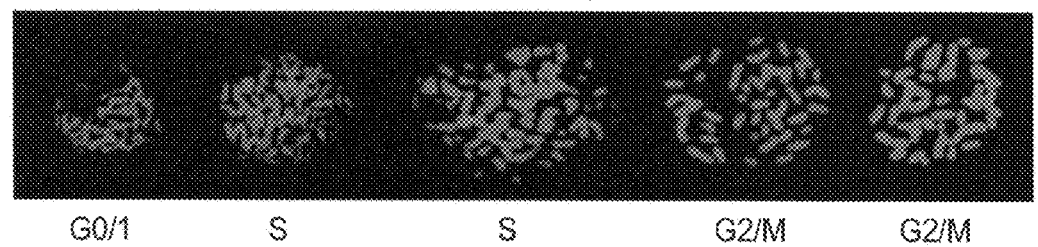

After the induction of PCC by Lasonolide A, cells were incubated in hypotonic solution (10 mM Tris-HCl [ph 7.4], 40 mM glycerol, 20 mM NaCl, 1 mM $CaCl_2$, 0.5 mM $MgCl_2$) at 37° C. for 15 min. Then followed with cytospining at 1,800 rpm for 10 min and normal PI staining as above (FIG. 1E).

Example 3

DNase I Sensitivity Assay

Cells were treated with different concentrations of Lasonolide A for 1 h and were collected with centrifuging. The centrifuged cells were washed with PBS and fixed with 1.5% PFA for 15 min on ice. After washing by PBS, fresh PBS was added (300 μL) to re-suspend the pellet, then 700 μL 70% EtOH was gently added and the mixture was maintained at −20° C. overnight. The solution was washed by PBS once, then washed by 1× DNase I reaction buffer (500 μL), then incubated in 200 μL Reaction buffer with 4 Units DNase I (2 μL), 37° C., 10 min. The solution was washed by PBS and incubated in 100 μL Polymerase reaction buffer including 16 μM dATP, 16 μM dCTP, 16 μM dGTP, 16 μM dUTP-FITC, 100 unit/mL Polymerase I, 37° C. 60 min. FL1 channel of Green fluorescence signal were measured with flow cytometer (FIG. 1C).

Example 4

Cell Cycle Analysis

Figure 2A:
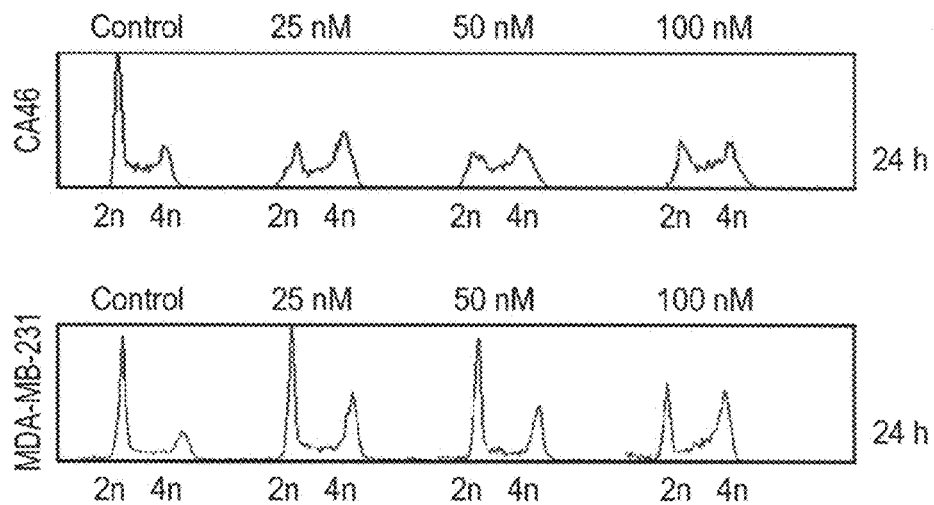
FIG. 2. Lasonolide A induces G2/M arrest and decreases BrdU incorporation: Long-time treatment (24 h) of Lasonolide A induced cell cycle arrest at G2/M phase in MDA-MB-231 cells and CA46 cells (A). At the same time, BrdU incorporation assay showed slow DNA replication post 24 h of Lasonolide A treatment (B) The data demonstrated that the PCC induction was the early events of Lasonolide A mechanisms.

After treatment, cells were collected, washed twice with ice-cold PBS, and fixed overnight with 70% precooled (−20° C.) ethanol. Fixed cells were resuspended in PBS containing 0.02 mg/mL RNase A (Roche, USA) and incubated at 37° C. for 15 min. Next, the cells were stained with 0.01 mg/mL propidium iodide (Sigma) in the dark at room temperature for 10 min. The DNA content was analyzed by flow cytometry using a FACSCalibur (Becton Dickinson, Sunnyvale, Calif.) with Cellquest and Modfit LT3.0 software (Becton Dickinson) (FIGS. 1D & 2A).

Example 5

BrdU Incorporation

Figure 2B:
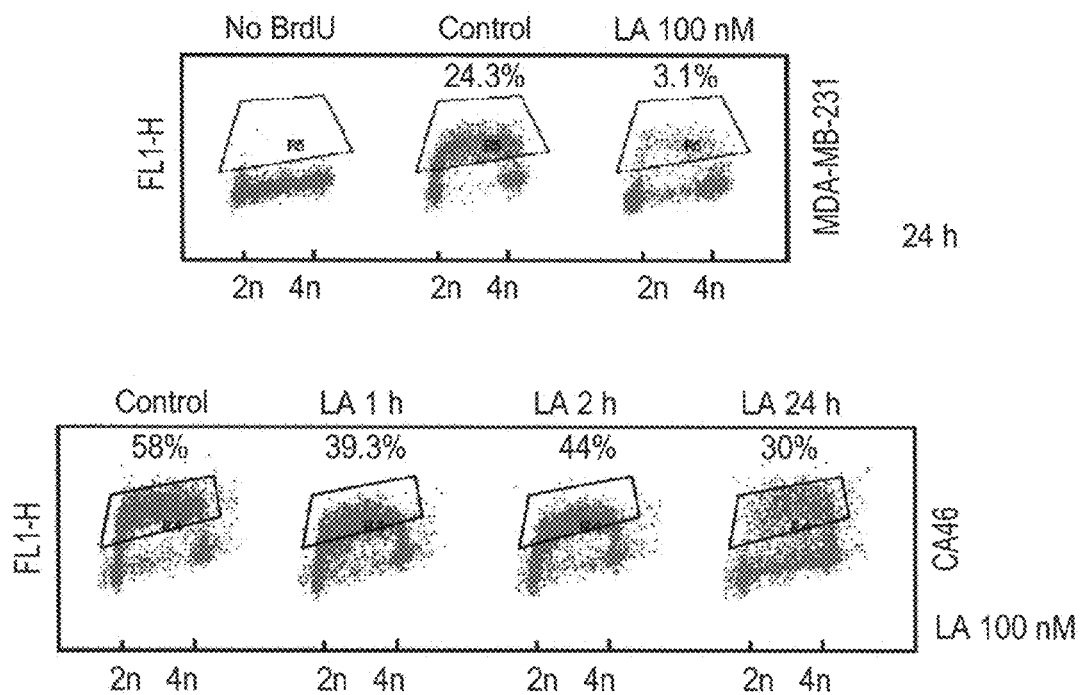

A number of cells ($5 \times 10^5$) were pulse-labeled with 50 μmol/L BrdU (Calbiochem, La Jolla, Calif.) for 30 minutes. Cells were collected, fixed in 70% ethanol at 4° C., washed with PBS, resuspended in 3 mL 2 mol/L HCl/0.5% Triton X-100, and left at room temperature for 30 minutes. Cells were spun down after adding 6 mL 0.1 M sodium borate (pH 8.5). Pellets were washed with PBS/0.5% Tween-20 twice, then resuspended in 15 μL FITC-conjuncted anti-BrdU antibody (Becton Dickinson, Franklin Lakes, N.J.). After incubation with the anti-BrdU antibody at room temperature for 60 minutes, pellets were washed once with PBS, and resuspended in 500 μL of PI solution (50 μg/mL PI and 50 μg/mL RNase). Analyses were done with a FACScan flow cytometer (Becton Dickinson, San Jose, Calif.) (FIG. 2B).

Example 6

In Vitro Phosphatase Activity Assays

Figure 3A:
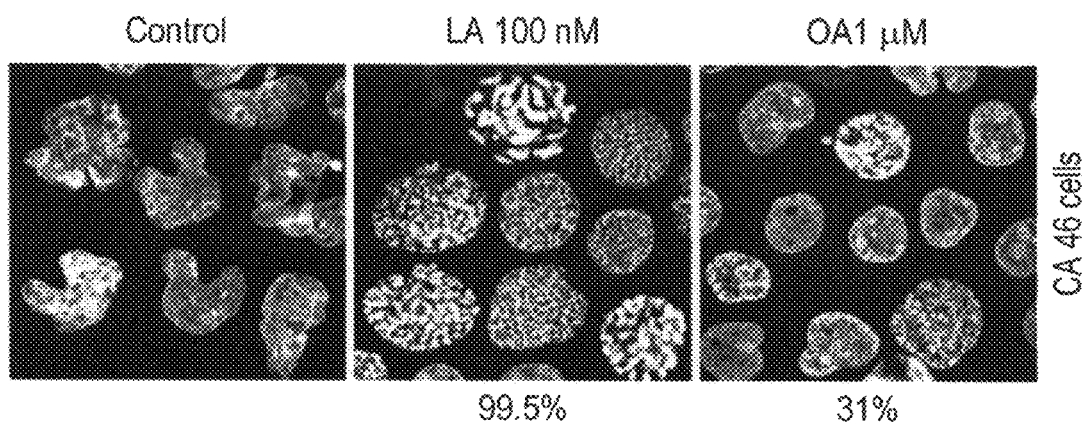
FIG. 3. Lasonolide A is a more potent PCC inducer than Okadaic Acid (OA), and has less inhibitory effect on phosphatase type 1 and 2A (PP1 and PP2A): 100 nM Lasonolide A or 1 μM OA treated CA46 cells for 1 h, comparing the efficiency of PCC induction, Lasonolide A had more potent ability than OA as 99.5% vs 31% (A). As for the induction of PCC in human lymphocytes, without additional reagents, 200 nM Lasonolide A resulted in 35.5% of lymphocytes going to PCC, and 1 μM OA induced 1.7% (B). Lasonolide A showed weaker inhibitory effect on PP2A and PP1. The $IC_{50}$ of Lasonolide A demonstrated that it is not a typical phosphatase inhibitor (C, D).
Figure 3B:
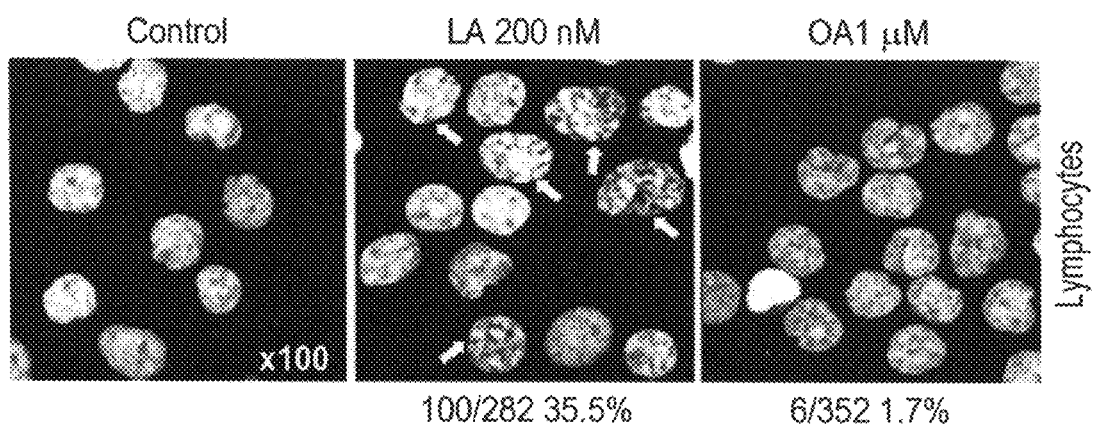
Figure 3C:
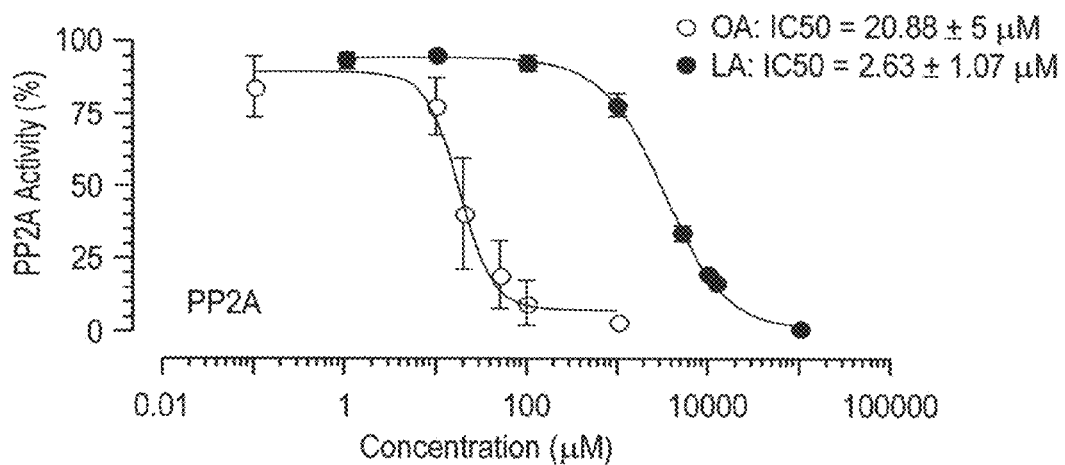
Figure 3D:
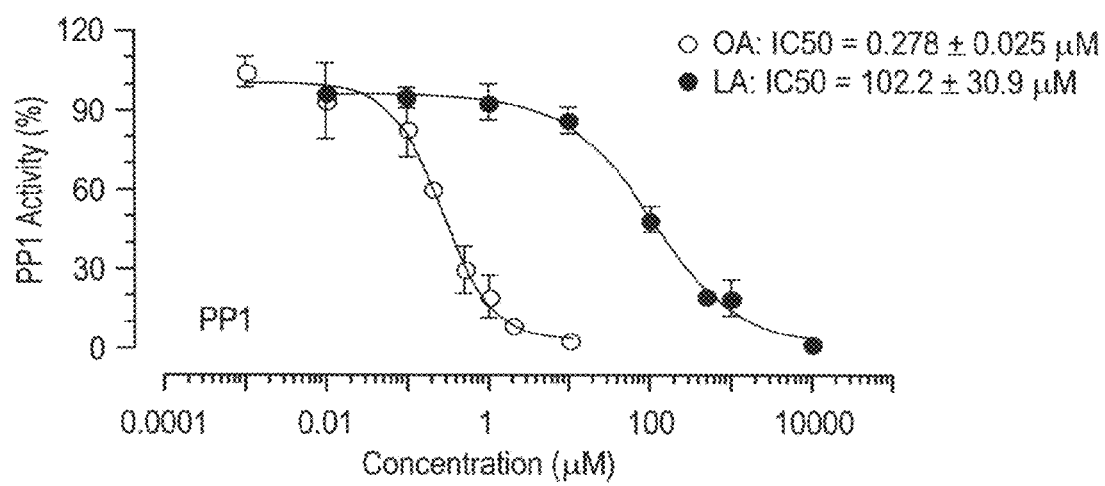

The inhibitory effect of active agents on PP2A or PP1 enzyme activity was determined by measuring the generation of free $PO_4$ from the phosphopeptide RRA(pT)VA, using the molybdate-malachite green-phosphate complex assay. The phosphatase assay was performed in a PP2A-specific reaction buffer [50 mM imidazole (pH 7.2), 0.2 mM EGTA, 0.02% 2-mercaptoethanol, 0.1 mg/mL of bovine serum albumin] using 10 μ/M phosphopeptide substrate and 0.03 Units PP2A (Upstate), or in PP1-specific reaction buffer [50 mM HEPES, 2 mM Dithiothreitol, 0.025% Tween-20, 0.1 mM EGT 100 mM NaCl] together with 100 μM phosphopeptide substrate and 0.03 Units PP1 (Biolabs). Different concentrations of active agents were added in the reaction system. After a 20-min incubation at 30° C., molybdate dye was added, and the amount of free phosphate generated was determined from the optical density at 630 nm (VERSAmax, Molecular Device), using a standard curve for free phosphate. Phosphatase activity was defined as picomoles of free $PO_4$ generated per minute per microgram of protein, and phosphatase activity without drug was defined as 100% (FIGS. 3C & 3D).

Example 7

Western Blot

Figure 4A:
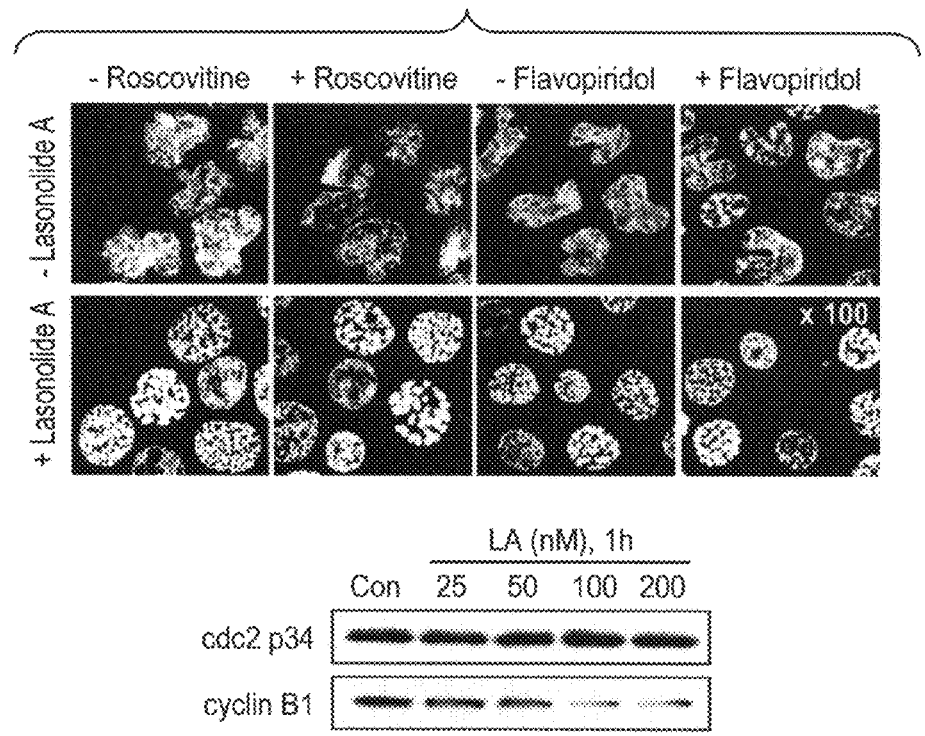
FIG. 4. Lasonolide A is different from the classical PCC inducer, and the PCC induction by Lasonolide A is independent of Cdk kinase and DNA replication, but related with topoisomerase II: Cdk inhibitor Roscovitine or Flavorpiridol could not influence the PCC induction by Lasonolide A. Lasonolide A decreased the protein level of cyclinB1 (A). The data showed that Lasonolide A acts differently with the typical PCC inducer. DNA replication inhibitor aphidicolin (B) had no effect on PCC induction by Lasonolide A, but topoisomerase II inhibitor ICRF187 (C) changed the pattern of PCC, which demonstrated that topoisomerase II was involved in the PCC induction by Lasonolide A.
Figure 4B:
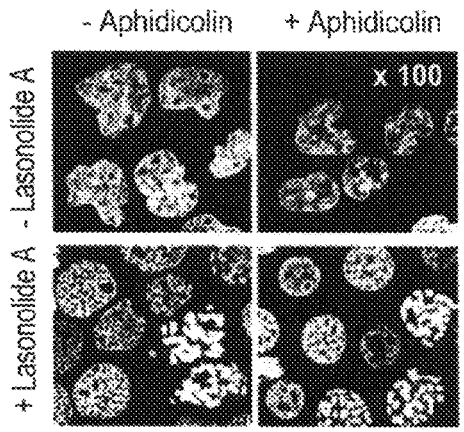
Figure 4C:
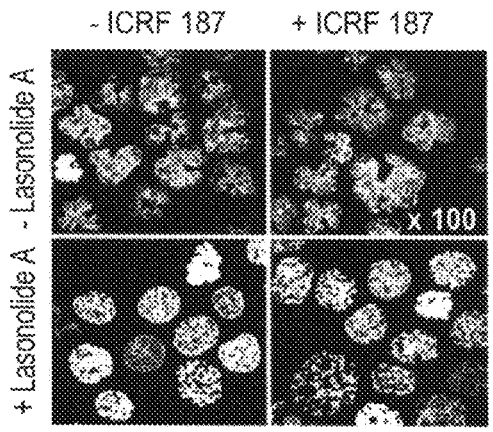
Figure 5A:
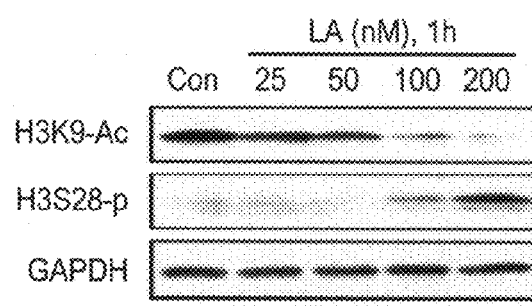
FIG. 5. Histone H3 modification might be involved in the induction of PCC induced by Lasonolide A: Lasonolide A decreased the acetylation of H3 (Arg9) and increased the phosphorylation of H3 (Ser28) (A). Lasonolide A also attenuated the enhancement of H3 acetylation induced by the HDAC inhibitor, SAHA (B). The induction of H3 acetylation with SAHA could inhibit the Lasonolide A-induced PCC partly (C), which suggested that H3 acetylation was involved in the PCC induction induced by Lasonolide A. Immunofluorescence assay showed the phosphorylation of H3 (Ser28) after Lasonolide A treatment (D).
Figure 5B:
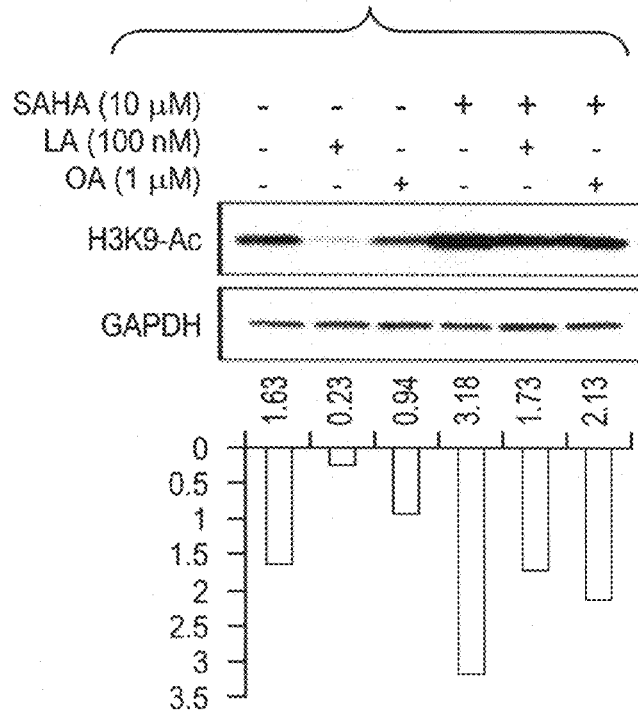
Figure 5C:
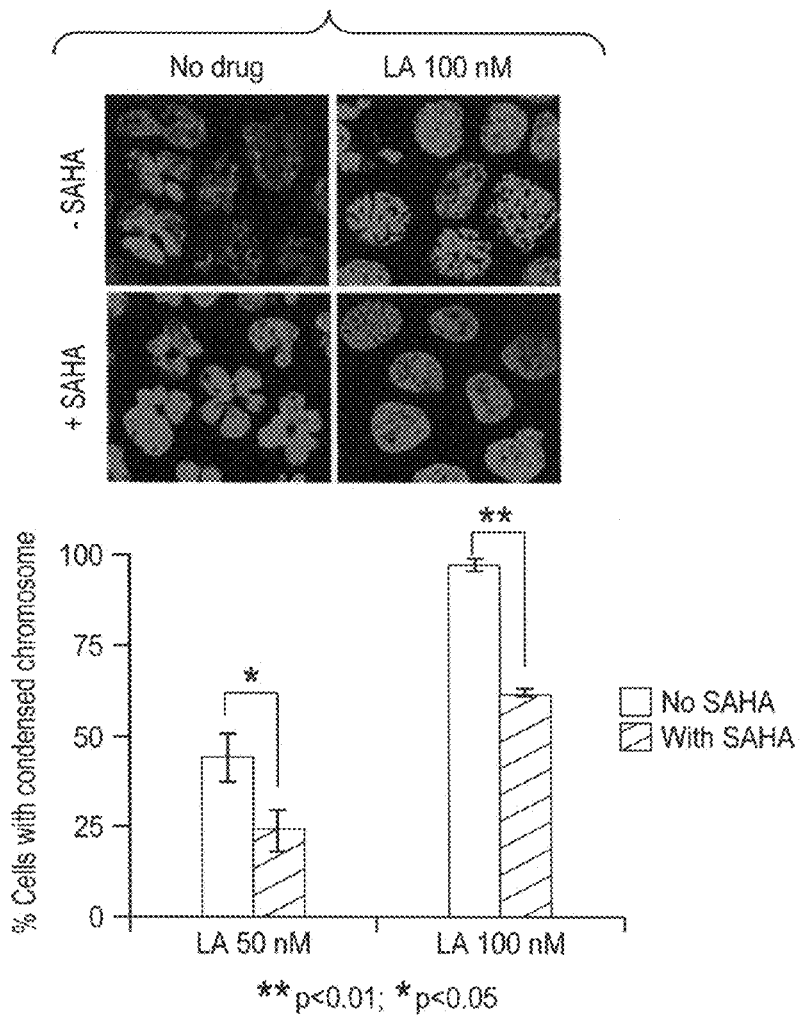
Figure 5D:
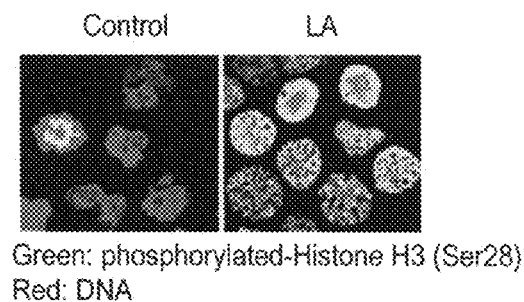

Protein levels were measured by Western blotting with corresponding specific primary antibodies, including those against Cdc2 p34(Santa Cruz), cyclinB1 (Santa Cruz) (FIG. 4A), Anti-Acetylated-$H3K_9$ (Upstate), phosphorylated-H3 Ser28 (Cell signaling). GAPDH was as the loading control.

Example 8

Immunofluorescence Assays

After drug treatments, CA46 cells were cytospun on the slides. Slides were fixed for 20 min with 4% paraformaldehyde in PBS (pH 7.4), and washed twice with PBS. After incubation for 20 min with 70% ethanol and washing with PBS, the cells were incubated in blocking buffer [8% bovine serum albumin (BSA) in PBS] for 1 h before incubation for 2 h with primary antibodies against phosphorylated-H3 Ser28 (Cell signaling) (FIG. 5). Slides were incubated for additional 1 h with the Alex488-conjugated secondary antibody (Alexa Fluoro 488 donkey anti-goat IgG, Molecular Probes, Invitrogen, CA). After three washes in PBS, cells were stained with 0.5 µg/mL propidium iodide (PI) and 100 µg/mL RNase A (Sigma, Mo.) for 15 min in the dark. Finally, slides were washed with PBS for three times and mounted with Vectashield anti-fade mounting media (Vector Laboratories, Inc., Burlingame, Calif.). Images were taken using a Nikon Eclipse TE-300 confocal microscope.

Cells were fixed with 4% paraformaldehyde and permeabilized with PBS containing 0.1% Triton X-100. After blocking with 1% bovine serum albumin for 30 min. Cells were incubated with Alexa Fluor 488-conjugated phalloidin (Molecular Probes) to stain actin stress fibers.

Example 9

Cell Adhesion Assay

Figure 6A:
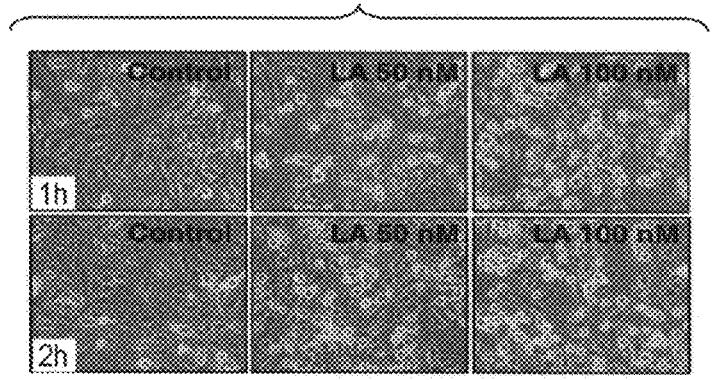
FIG. 6. Lasonolide A inhibits adhesion and migration of MDA-MB-231 cells: Low dose and short-time treatment of Lasonolide A on MDA-MB-231 cells detached cells into suspension (A). Lasonolide A also reduced cells' attachment to collagen I or fibronectin (B). The migration of MDA-MB-231 cells was inhibited by Lasonolide A as shown in transwell migration assay. Lasonolide A reorganized the actin network in MDA-MB-231 cells (C).
Figure 6A:
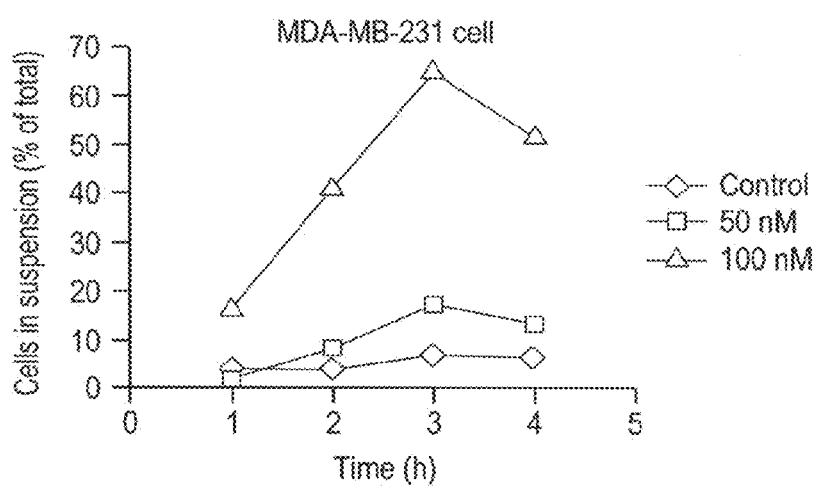
Figure 6B:
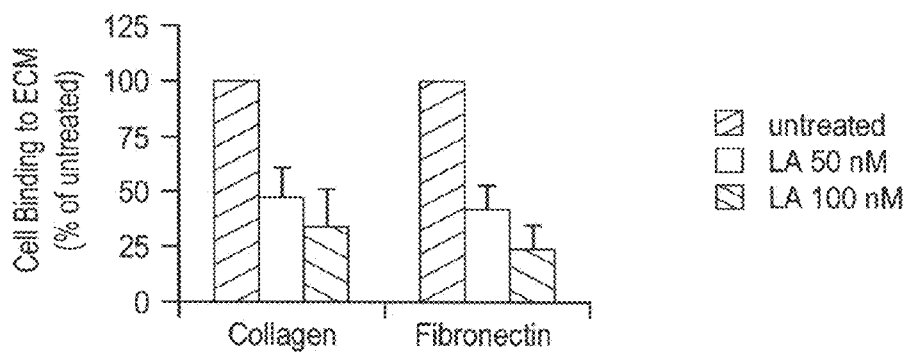
Figure 6C:
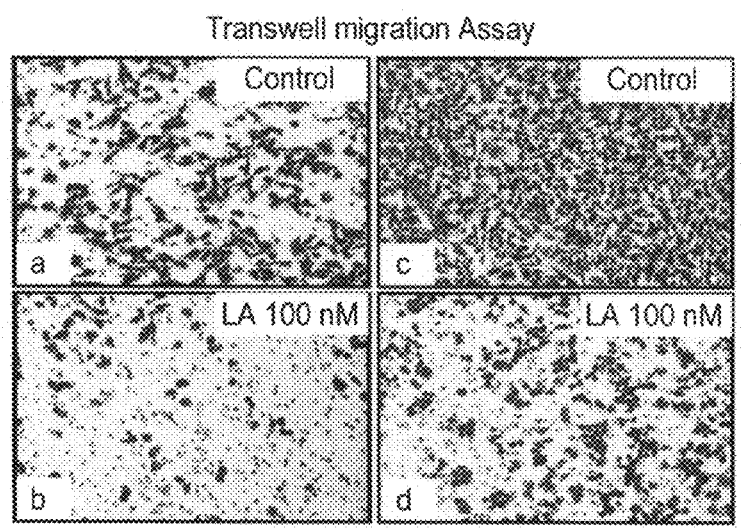
Figure 6D:
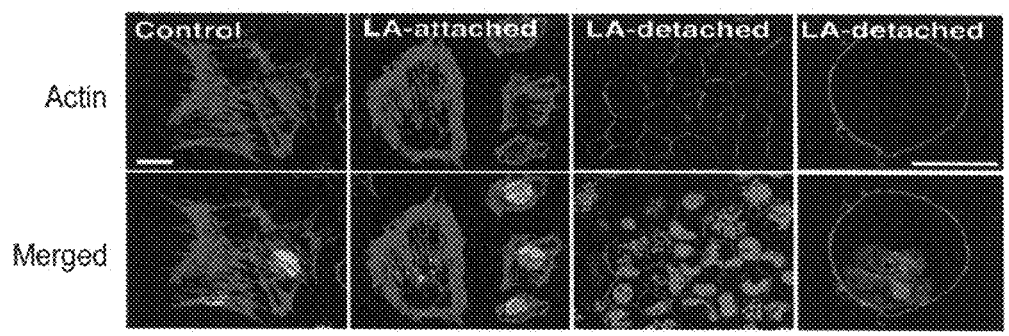

The effect of Lasonolide A on the extracellular matrix-induced cell adhesion was determined as follows. Fibronectin or collagen was diluted in sterile water and applied to 96-well plates overnight at 4° C. Nonspecific binding sites were blocked with 1% bovine serum albumin for 1 h at room temperature. Breast cancer MDA-MB-231 cells were serum starved for 45 min, detached with 2 mmol/L EDTA in PBS, plated in triplicate onto wells in serum-free medium with or without Lasonolide A, and allowed to adhere for 1 h at 37° C. Nonadherent cells were washed away and adherent cells were fixed with 4% paraformaldehyde and stained with 0.1% crystal violet in 2% methanol. Following extensive washing with tap water, dye was extracted with 10% acetic acid and quantified by measuring absorbance at 595 nm on a multiwell spectrophotometer (VersaMax, Molecular Devices). (FIGS. 6A, 6B, & 6D)

Example 10

Transwell Migration Assay

The effect of Lasonolide A on the migration of breast cancer MDA-MB-231 cells was determined in a transwell Boyden Chamber (Costar, Mass.) using a polycarbonate filter with a pore size of 81 m, which was coated with 0.2% gelatin, balancing with gelatin at 37° C. for 1 h, then removal of the gelatin and covering with DMEM without serum overnight at 37° C. In the standard assay, after removing medium, 0.1 mL of cell suspension (1×10⁵ cells/ml, in serum-free medium) with Lasonolide A or 0.1% DMSO (v/v) was added to the upper compartment of the chamber. The lower compartment contained 0.6 mL of DMEM medium supplemented with 20% serum. After incubation for 6 h at 37° C., the filter was removed and fixed with ethanol. Cells remaining on the upper surface of the filter (non-migrated) were scraped gently. Then, migrated cells on the lower surface of the filter were stained with 0.1% crystal violet and taken photographs under microscope (FIG. 6C).

The endpoints of all ranges directed to the same component or property are inclusive of the endpoint and independently combinable.

The contents of all references (including literature references, issued patents, published patent applications, and co-pending patent applications) cited throughout this application are hereby expressly incorporated herein in their entireties by reference.

Those skilled in the art will recognize, or be able to ascertain using no more than routine experimentation, many equivalents of the specific embodiments of the invention described herein. Such equivalents are intended with be encompassed by the following claims.

What is claimed is:

1. A method of stimulating chromosome condensation in a cell, and observing chromosome condensation in the cell, wherein chromosome condensation is observed by a chromosome spread assay, a DNase I sensitivity assay, a phosphatase activity assay, an immunofluorescence assay, a cell adhesion assay, or a transwell migration assay;

and the compound is chosen from

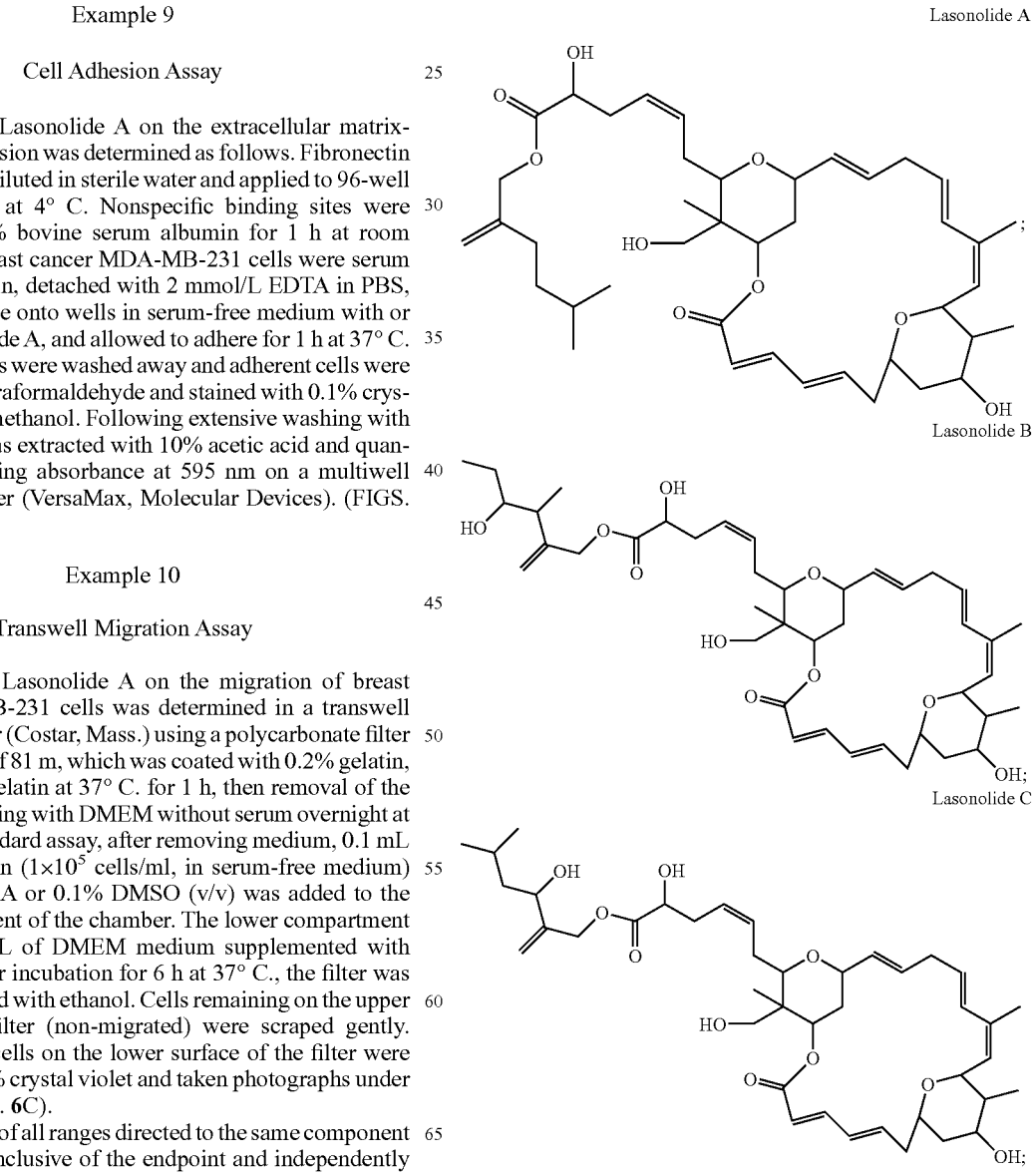

-continued

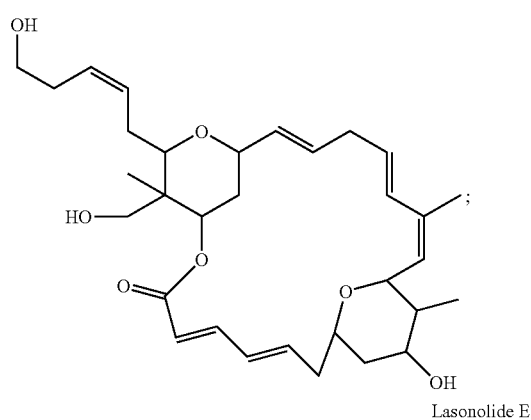
Lasonolide D

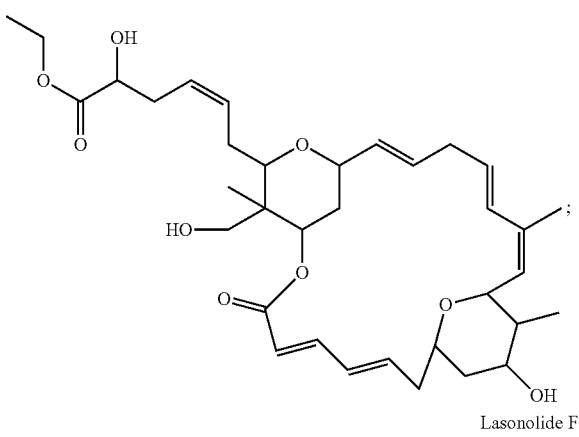
Lasonolide E

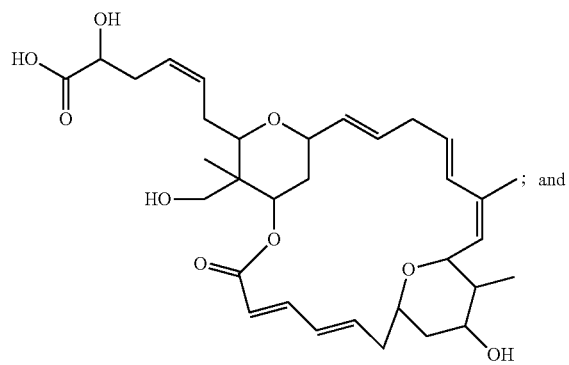
Lasonolide F

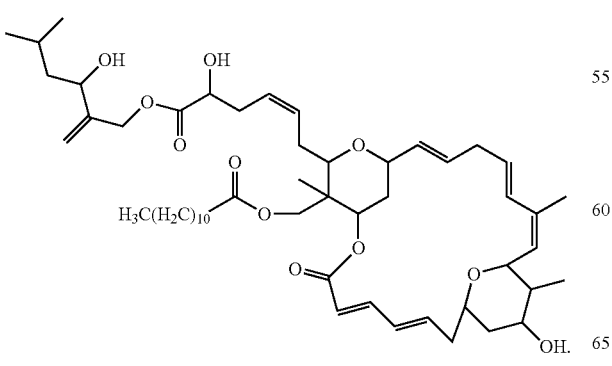
Lasonolide G

2. The method of claim 1 wherein the chromosome condensation is observed by a phosphatase activity assay, an immunofluorescence assay, a cell adhesion assay, or a transwell migration assay.

3. The method of claim 1 wherein the cells are contacted in vitro.

4. The method of claim 3 wherein the cells are proliferating cells; and the concentration of the compound is from about 1 nM to about 100 nM.

5. The method of claim 1 wherein the cells are proliferating cells, the cells are contacted in vivo by administering the compound to a subject; and the Cmax of the compound of formula (I) is at least 1 nM.

6. A method of analyzing human cell chromosomes by causing premature chromosome condensation, which comprises:

(a) incubating a cell in vitro with a medium comprising a lasonolide derivative chosen from

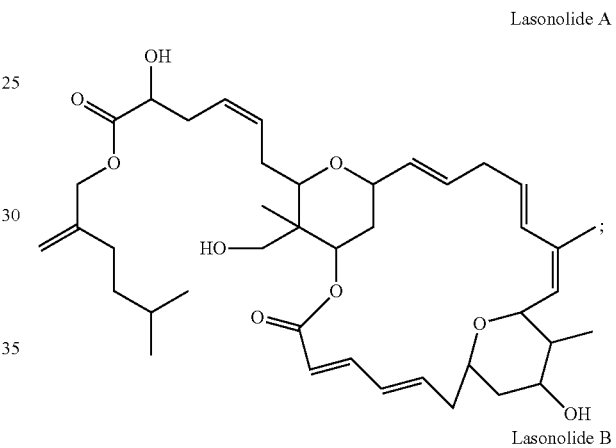
Lasonolide A

Lasonolide B

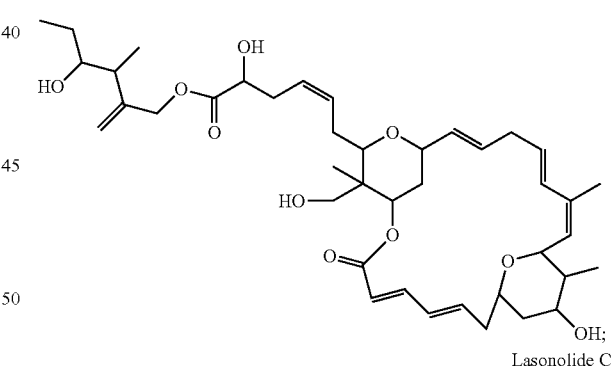
Lasonolide C

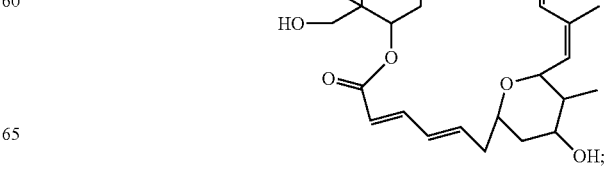

-continued

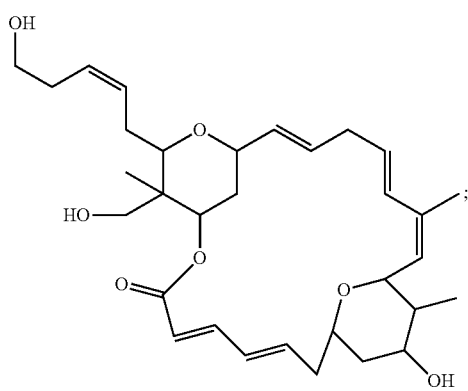
Lasonolide D

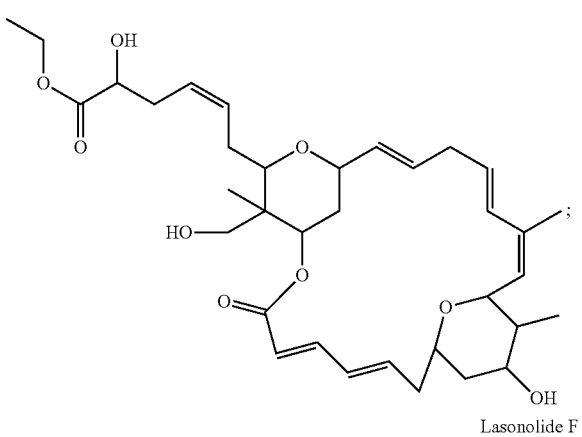
Lasonolide E

Lasonolide F

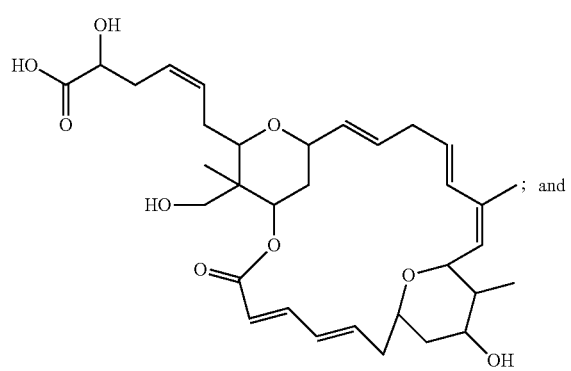
Lasonolide G wherein the lasonolide derivative is present in an amount effective to induce premature chromosome condensation (b) analyzing the chromosomes treated in step a);

wherein analyzing the chromosome comprises preparing a chromosome spread of the treated chromosomes; or hybridizing a detectable oligonucleotide to at least one or more chromosomes and enumerating chromosome spots.

7. The method of claim 6 wherein the detectable oligonucleotide is an oligonucleotide bound to a fluorescent moiety or bound to a moiety selected from a group consisting of biotin, digoxigenin, antigens, enzymes and haptens.

8. A culture medium for inducing premature chromosome condensation in a cell comprising a lasonolide derivative having mitosis enhancing properties present in an amount effective to induce premature chromosome condensation; wherein the lasonolide derivative is a selected from

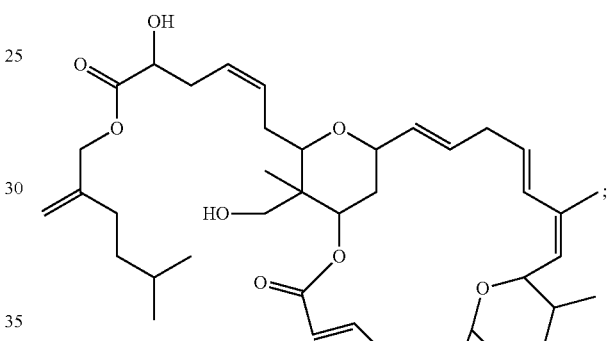
Lasonolide A

Lasonolide B

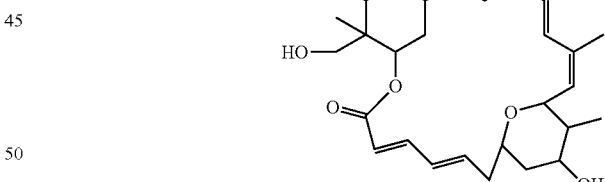
Lasonolide C

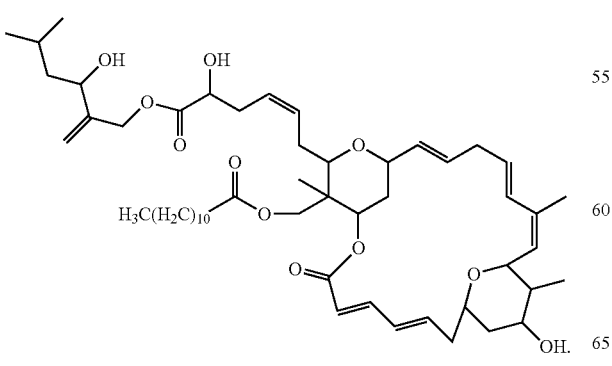

Lasonolide D

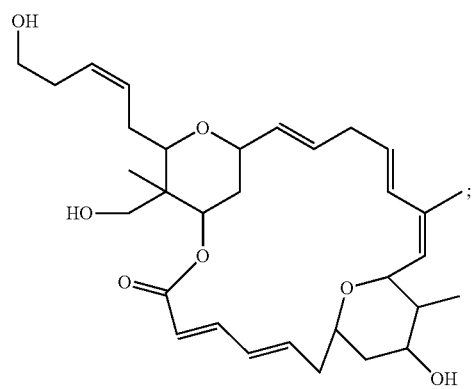

Lasonolide E

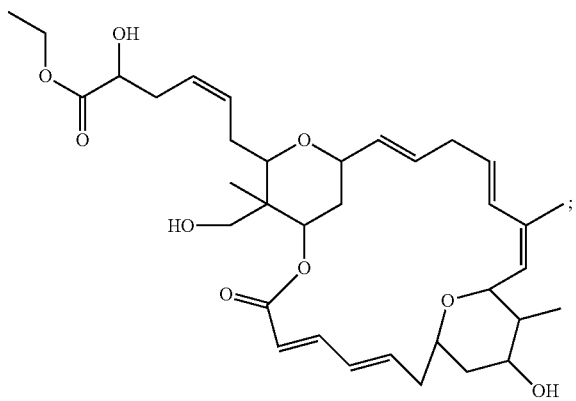

Lasonolide F

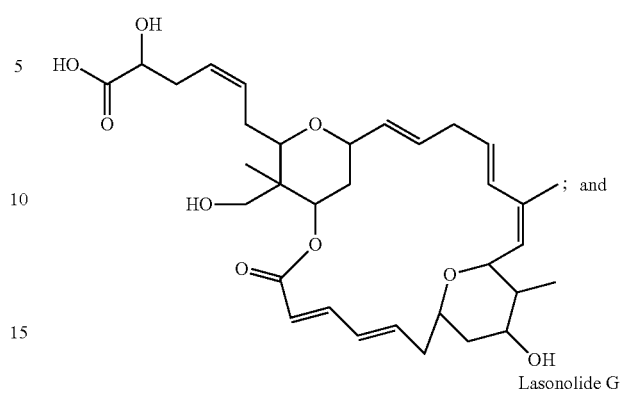

Lasonolide G

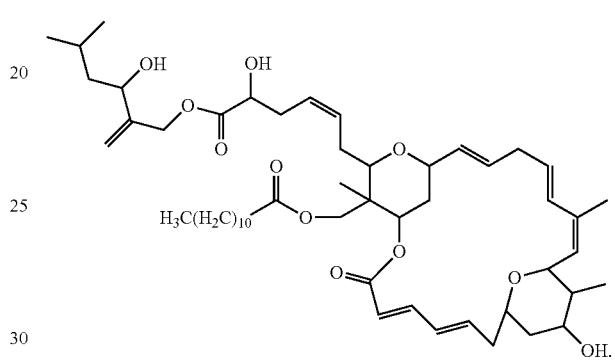

further comprising a phosphatase inhibitor selected from a group consisting of okadaic acid, salts of okadaic acid, calyculin A, cantharidic acid, cantharidin, cypermethrin, deltamethrin, dephostatin, 3,4-dephostatin, endothall, fenvalerate, fostriecin, microcystin-LA, microcystin-LF, microcystin-LR, microcystin-LW, microcyctin-RR, and microcystin-YR.

* * * * *